United States Patent
Lambert et al.

(10) Patent No.: US 6,660,286 B1
(45) Date of Patent: *Dec. 9, 2003

(54) EMULSION VEHICLE FOR POORLY SOLUBLE DRUGS

(75) Inventors: Karel J. Lambert, Woodinville, WA (US); Panayiotis P. Constantinides, Bothell, WA (US); Alexander K. Tustian, Bothell, WA (US); Steven C. Quay, Edmonds, WA (US)

(73) Assignee: Sonus Pharmaceuticals, Inc., Bothell, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/317,499

(22) Filed: May 24, 1999

Related U.S. Application Data

(63) Continuation-in-part of application No. 09/003,173, filed on Jan. 5, 1998.
(60) Provisional application No. 60/048,840, filed on Jun. 6, 1997, and provisional application No. 60/034,188, filed on Jan. 7, 1997.

(51) Int. Cl.[7] ............................................. A01K 9/107
(52) U.S. Cl. ........................................ 424/405; 514/938
(58) Field of Search ..................... 514/772.2, 772.7, 514/937–38, 941, 962, 455, 405, 408

(56) References Cited

U.S. PATENT DOCUMENTS

| | | | |
|---|---|---|---|
| 4,439,432 A | 3/1984 | Peat | 424/240 |
| 4,551,332 A | 11/1985 | Stillman | |
| 4,578,391 A | 3/1986 | Kawata et al. | 514/256 |
| 4,784,845 A | 11/1988 | Desai et al. | |
| 4,797,285 A | 1/1989 | Barenholz et al. | |
| 4,898,735 A | 2/1990 | Barenholz et al. | |
| 4,960,814 A | 10/1990 | Wu et al. | 524/312 |
| 5,002,767 A | 3/1991 | Massë | |
| 5,041,278 A | 8/1991 | Janoff et al. | |
| 5,114,957 A | 5/1992 | Hendler et al. | |
| 5,179,122 A | 1/1993 | Greene et al. | 514/458 |
| 5,330,689 A | 7/1994 | Janoff et al. | |

(List continued on next page.)

FOREIGN PATENT DOCUMENTS

| | | | | |
|---|---|---|---|---|
| AU | B-24213/88 | 2/1992 | | A61K/37/02 |
| AU | B-70937/91 | 9/1994 | | A61K/31/355 |
| AU | B27266/92 | 4/1995 | | A61K/7/48 |

(List continued on next page.)

OTHER PUBLICATIONS

Alade, S. et al., *Polysorbate 80 and E–Ferol Toxicity*, Pediatrics vol. 77, No. 4 (1986).

Alkan–Onyuksel, H, et al. "*A Mixed Micellar Formulation Suitable for the Parenteral Administration of Taxol*", Pharmaceutical Research 2(2): 206–212 (1994).

Arrowsmith, J. et al., *Morbidity and Mortality Among Low Birth Weight Infants Exposed to an Intravenous Vitamin E Product, E–Ferol*, Pediatrics, vol. 873, No. 2 (1989).

(List continued on next page.)

Primary Examiner—Edward J. Webman
(74) Attorney, Agent, or Firm—Christensen O'Connor Johnson Kindness PLLC

(57) ABSTRACT

An emulsion of tocopherol incorporating a co-solvent and, stabilized by biocompatible surfactants, as a vehicle or carrier for therapeutic drugs, which is substantially ethanol free and which can be administered to animals or humans by various routes is disclosed. Also included in the emulsion is PEGylated vitamin E. PEGylated α-tocopherol includes polyethylene glycol subunits attached by a succinic acid diester at the ring hydroxyl of vitamin E and serves as a primary surfactant, stabilizer and a secondary solvent in emulsions of α-tocopherol.

22 Claims, 4 Drawing Sheets

U.S. PATENT DOCUMENTS

| | | |
|---|---|---|
| 5,387,579 A | 2/1995 | Maybeck et al. |
| 5,391,377 A | 2/1995 | Barnwell |
| 5,407,683 A | 4/1995 | Shively ............... 424/439 |
| 5,478,860 A | 12/1995 | Wheeler et al. ......... 514/449 |
| 5,504,102 A | 4/1996 | Agharkar et al. ........ 514/449 |
| 5,532,002 A | 7/1996 | Story |
| 5,534,499 A | 7/1996 | Ansell |
| 5,573,781 A | 11/1996 | Brown et al. |
| 5,583,105 A | 12/1996 | Kovacs et al. |
| 5,614,549 A | 3/1997 | Greenwald et al. |
| 5,616,330 A | 4/1997 | Kaufman et al. ......... 424/400 |
| 5,621,001 A | 4/1997 | Canetta et al. ........... 514/449 |
| 5,626,869 A | 5/1997 | Nyqvist et al. .......... 424/450 |
| 5,648,506 A | 7/1997 | Desai et al. |
| 5,653,998 A | 8/1997 | Hamann et al. |
| 5,681,846 A | 10/1997 | Trissel |
| 5,683,715 A | 11/1997 | Boni et al. ............. 424/450 |
| 5,726,181 A | 3/1998 | Hausheer et al. |
| 5,733,526 A * | 3/1998 | Trevino et al. |
| 5,877,205 A | 3/1999 | Andersson ............ 514/449 |

FOREIGN PATENT DOCUMENTS

| | | | |
|---|---|---|---|
| EP | 0 001 851 | 5/1979 | ........... A61K/9/00 |
| EP | 0 299 528 | 7/1988 | .......... A61K/31/71 |
| EP | 0 427 582 A2 | 5/1991 | |
| EP | 0 546 951 | 12/1992 | .......... A61K/37/02 |
| EP | 0 382 779 B1 | 8/1993 | .......... A61K/37/20 |
| EP | 0382 779 B1 | 8/1993 | .......... A61K/37/20 |
| EP | 0 700 679 A1 | 8/1995 | .......... A61K/9/127 |
| EP | 0 712 631 A2 | 5/1996 | .......... A61K/38/13 |
| EP | 0 474 647 B1 | 2/1997 | ........... A61L/15/44 |
| EP | 0 988 858 A1 | 3/2000 | |
| WO | WO 88/06442 | 9/1988 | ........... A61K/9/66 |
| WO | WO 89/03689 | 5/1989 | .......... A61K/37/20 |
| WO | WO 92/13531 | 8/1992 | ......... A61K/31/355 |
| WO | WO 94/12154 | 6/1994 | .......... A61K/9/127 |
| WO | WO 94/20143 | 9/1994 | .......... A61K/47/02 |
| WO | WO 95/01785 | 1/1995 | ........... A61K/9/48 |
| WO | WO 95/11039 | 4/1995 | .......... A61K/38/13 |
| WO | WO 95/20943 | 8/1995 | .......... A61K/9/127 |
| WO | WO 95/24892 | 9/1995 | ........... A61K/9/12 |
| WO | WO 95/25504 | 9/1995 | .......... A61K/9/107 |
| WO | WO 95/31217 | 11/1995 | .......... A61K/47/22 |
| WO | WO 96/15774 | 5/1996 | .......... A61K/9/127 |
| WO | WO 96/17593 | 6/1996 | .......... A61K/9/107 |
| WO | WO 96/17594 | 6/1996 | .......... A61K/9/107 |
| WO | WO 96/17899 | 6/1996 | .......... C09K/15/04 |
| WO | WO 96/22103 A1 | 7/1996 | |
| WO | WO 96/32094 | 10/1996 | .......... A61K/9/127 |
| WO | WO 96/33697 | 10/1996 | .......... A61K/9/107 |
| WO | WO 96/33987 | 10/1996 | ......... C07D/311/72 |
| WO | WO 96/40056 | 12/1996 | .......... A61K/9/107 |
| WO | WO 97/03651 | 2/1997 | .......... A61K/9/107 |
| WO | WO 97/07113 | 2/1997 | ........ C07D/311/72 |
| WO | WO 97/09964 | 3/1997 | .......... A61K/9/107 |
| WO | WO 97/10849 | 3/1997 | .......... A61K/47/34 |
| WO | WO 97/11682 | 4/1997 | .......... A61K/9/107 |
| WO | WO 97/13528 | 4/1997 | .......... A61K/47/14 |
| WO | WO 97/14705 | 4/1997 | ........... C07F/9/655 |
| WO | WO 97/22358 | 6/1997 | .......... A61K/38/13 |
| WO | WO 97/23192 | 7/1997 | ............ A61K/7/00 |
| WO | WO 97/28151 | 8/1997 | ........ C07D/311/72 |
| WO | WO 97/30695 | 8/1997 | .......... A61K/9/107 |
| WO | WO 97/29773 | 9/1997 | .......... A61K/39/39 |
| WO | WO 97/33552 | 9/1997 | ............ A61K/5/00 |
| WO | WO 97/36611 | 10/1997 | .......... A61K/38/13 |
| WO | WO 97/44124 | 11/1997 | ........... B01J/13/00 |
| WO | WO 97/46204 | 12/1997 | |
| WO | WO 98/00110 | 1/1998 | .......... A61K/9/107 |
| WO | WO 98/00128 | 1/1998 | ......... A61K/31/335 |
| WO | WO 98/08597 | 3/1998 | ........... B01F/17/34 |
| WO | WO 98/11902 | 3/1998 | .......... A61K/31/71 |
| WO | WO 98/18321 | 5/1998 | .......... A01N/25/30 |
| WO | WO 98/21197 | 5/1998 | ......... C07D/311/00 |
| WO | WO 98/30204 A1 | 7/1998 | |
| WO | WO 98/30204 | 7/1998 | .......... A61K/9/107 |
| WO | WO 98/30205 A1 | 7/1998 | |
| WO | WO 98/37869 | 9/1998 | .......... A61K/9/107 |
| WO | WO 98/40051 | 9/1998 | .......... A61K/9/107 |
| WO | WO 98/40094 | 9/1998 | .......... A61K/38/13 |

OTHER PUBLICATIONS

Balistreri, W. et al., *Lessions from the E–Ferol Tragedy*, Pediatrics vol. 78, No. 3 (1986).

Bateman N.E., et al., "*Kinetics of D–α–tocopherol in a water soluble base in man*" J. Pharm. Pharmacol. 37:728–729 (1985).

Bignami, G. et al., *Biological Activity of 26–succinylbryostatin 1*, Biochimica et Biohphysica Acta 1312 (pp. 197–206, (1996).

Brunzell, J. D., et al, "*Pathophysiology of Lipoprotein Transport*", Metabolism 27(9): 1109–1127 (1976).

Cherng–Chyi Fu, R., et al., "*The Biocompatibility of Parenteral Vehicles–In Vitro/In Vivo Screening Comparison and the Effect of Excepients on Hemolysis*", J. Parenter. Sc. Tech., 41(5): 164–168 (1987).

Chun Li, et al; *Complete Regression of Well–established Rumors Using a Novel Water–Soluble Poly(1–Glutamic Acid)–Paclitaxel Conjugate*, Cancer Research 58, pp. 2404–2409, (1998).

Constantinides, P., *Lipid Microemulsions for Improving Drug Dissolution and Oral Absorption: Physical and Biopharmaceutical Aspects*, Pharmaceutical Research, vol. 12, No. 11 (1995).

Coon, J. et al., *Solutol HS 15, Nontoxic Polyoxyethylene Esters of 12–Hydroxystearic Acid, Reversis Multidrug Resistance*, Cancer Research 51, pp. 897–902 (1991).

Dasgupta, J., et al., *Vitamin E, Its Status and Role in Leukemia and Lymphoma*, Neoplasma, Vol 40, No. 4 (1993).

Davis, S., et al., *Lipid Emulsions as Drug Delivery Systems*, Annals New York Academy of Sciences, pp. 75–84.

Eastman Vitamin E TPGS, "*Products and Applications*", Eastman Chemical Company Publication EFC–226 (1996).

Farah, N., et al., *Self–Microemulsifying Drug Delivery Systems for Improving In–Vitro Dissolution of Drugs*, Gattefosse s.a. PF 9386, No. 173.

Fariss, M., et al., *The Selective Antiproliferative Effects of α–Tocopheryl Hemisuccinate and Cholesteryl hemisuccinate on Murine Leukemia Cells Result from the Action of the Intact Compounds*, Cancer Research 54, pp. 3346–3351, (1994).

Geetha, A., et al., α–*Tocopherol Reduces Doxorubicin–Induced Toxicity in Rates—Histological and Biochemical Evidences*, Ind. J. Physiol. Pharmac, 34(2), pp. 94–100 (1990).

Hadfield, J.I.H., "*Preoperative and Postoperative Intravenous Fat Therapy*", Hadfield: Intravenous Fat Therapy, Brit. J. Surg. 52(4):291–298 (1965).

Hansrani, P.K., et al, "*The Preparation and Properties of Sterile Intravenous Emulsions*" J. Parenter. Sc. Tech. 37:145–150 (1983).

Heird, W. C., et al., "*Total parenteral nutrition*", Medical Progress, J. of Pediatrics 86(2):2–16 (1975).

Hidiroglou, M., et al., "Pharmacokinetic disposition in sheep of various vitamin E preparations given orally or intravenously", British J. of Nutrition, 59:509–518 (1988).

Ingold, K. U., et al., Autoxidation of lipids and antioxidation by α–tocopherol and ubiquinol in homogeneous solution and in aqueous dispersions of lipids: Unrecognized consdquences of lipid particle size as exemplified by oxidation of human low density lipoprotein, Proc. Natl. Acad. Sci. USA, 90:45–49 (1993).

Israel, K., et al., RRR–α–Tocopheryl Succinate Inhibits the Proliferation of Human Prostatic Tumor Cells with Defective Cell Cycle/Differentiation Pathways, Lawrence Erlbaum Assoicates, Inc., vol. 24, No. 2, (1995).

Kagkadis, K. A., et al., "A Freeze–Dried Injectable Form of Ibuprofen: Development and Optimisation Using Response Surface Methodology", 560(5) :317 (1996).

Kato, Y., et al., Blood Clearance and tissue Distribution of Various Formulations of α–Tocopherol Injection After Intravenous Administration, Chem. Pharm. Bull. 41(3) pp. 599–605 (1993).

Kelloff et al., "Clinical Development Plan: Vitamin E", J. Cellular Biochem. Suppl. 20:282–299.

Kleinerman, E. et al., Activation of Tumoricidal Properties in Human Blood Monocytes by Liposomes Containing Lipophilic Muramyl Tripeptide, Cancer Reserach, Vol 43, pp. 2010–2014, (1983).

Klostergaard, J., Macrophage Tumoricidal Mechanisms, 50th Forum in Immunology.

Kurihara, A., et al., Enhanced Tumor Delivery and Antitumor Activity of Palmitoyl Rhizoxin Using Stable Lipid Emulsions in Mice, Pharmaceutical Reserach, vol. 13, No. 2 (1996).

Lidgate, D., et al., Sterile Filtration of a Parenteral Emulsion, Pharmaceutical Research, vol. 9, No. 7, (1992).

Lundberg, B., A Submicron Lipid Emulsion Coated with Amphipathic Polyethylene Glycol for Parenterial Administration of Paclitaxel (Taxol), J. Pharm. Pharmacol. Vol 49, pp. 116–121 (1997).

Lundberg, B., Preparation of Drug–Carrier Emulsions Stabilized with Phosphatidylcholine–Surfactant Mixtures, Journal of Pharmaceutical Sciences, vol., 83, No. 1, (1994).

Matilla, M.A.K., et al., "Intravenous premedication with diazepan", Anaesthesia, 39:879–882 (1984).

Meng, H.C., "Use of Fat Emulsions in Parenteral Nutrition", I.V. Additive Review, Drug Intelligence and Clinical Pharm. 6:321–330 (1972).

Microemulsions: Formulation Guide, Gattefosse, PF 9225A (1994).

Myers, S., et al., Preparation and Characterization of Emulsifiable Glasses: Oil–in–Water and Water–in–Oil–Water Emulsions, Journal of Colloid and Interface Science, vol. 149, No. 1, (1992).

Nakamoto, Y., et al., Studies on Pharmaceutical Modification of Anticancer Agents. Enhancement of Lymphatic Transport of Mitomycin C by Parenterial Emulsions, Chem. Pharm. Bull. vol. 23, No. 10 pp. 2232–2238 (1975).

Ojima, I, et al., Syntheses and Structure–Activity Relationships of the Second–Generation Antitumor Taxoids: Exceptional Activity Against Drug–Resistant Cancer Cells, J. Med. Chem. vol. 39, pp. 3889–3896 (1996).

Prankerd, R.J., et al., "Preliminary Development and Evaluation of a parenteral Emulsion Formulation of Penclomedine (NSC–338720;3, 5–dichloro–2, 4–dimethoxy–6–trichloromethylpyridine): A novel, Practically Water Insoluble Cytotoxic Agent", J. Parenter. Sc. Tech. 42:76–81 (1988).

Prankerd, R.J., et al., "The Use of Oil–in–Water Emulsions as a Vehicle for Parenteral Drug Administration", J. Parenter. Sc. Tech., 44:139–149 (1990).

Prasad, K., et al., Modification of the Effect of Tamoxifen, cis–Platin, DTIC, and Interferon–α2b on Human Malanoma Cells in Culture by a Mixture of Vitamins, Lawrence Erlbaum Associates, Inc., vol. 24, No. 3, pp. 233–245, (1994).

Remington's Pharmaceutical Sciences, Fifteenth Edition, (1975).

Saladino, C., et al., Platelet Aggregability in Rats with Early Atheroslerotic Changes Induced by Parenterally–Administered Lipid Emulsions, Atherosclerosis, vol. 66, pp. 19–28 (1987).

Simamora, P., et al: Emulsion Formulations for Intravenous Administration of PaclitaxelA Journal of Pharmaceutical Science & Technology, vol. 52, No. 4, (1998).

Singh, M. et al., "Parenteral Emulsions As Drug Carrier Systems", J. Parenter Sci. Tech., 40:34–41 (1990).

Sweetana, S., et al., "Solubility Principles and practices for Parenteral Drug Dosage Form Development", PDA J. Pharm. Sc. Tech., 50:(5):330–342(1996).

Takahashi, T., et al., Enhancement of the Cancer Chemotherapeutic Effect by Anticancer Agents in the Form of Fat Emulsion, Tohoku J. Exp. Med. vol. 123, pp. 235–246(1977).

Takeuchi, H., et al., Redispersible Dry Emulsion System as Novel Oral Dosage Form of Oily Drugs: In Vivo Studies in Beagle Dogs, Chem. Pharm. Bull. No. 39, Vol 12, pp. 3362–3364(1991).

Takeuchi, H., et al., Preparation of Powdered Redispersible Vitamin E Acetate Emulsions by Spray–Drying Technique, Chem. Pharm. Bull. vol. 39, No. 6, pp. 1528–1531 (1994).

Tarr, B., et al. A New Parenterial Emulsion for the Administration of Taxol, Pharmaceutical Research, vol. 4, No. 2 (1987).

Tengerdy R. P., et al., "Vitamin E adjuvant formulation in mice".

Urano, S., et al., Vitamin E: Inhibition of Retinol–Induced Hemolysis and Membrane–Stabilizing Behavior, Journal of Biological Chemistry, vol. 267, No. 26, pp. 18365–18370 (1992).

Wadleigh, R., et al., Vitamin E in the Treatment of Chemotherapy–Induced Mucositis, Americna Journal of Medicine, vol. 92, pp. 481–484 (1992).

Wheeler, J.J., et al., "Polyethylene Glycol Modified Phospholipids Stabilize Emulsions Prepared from Triacylglycerol", J. Pharm. Sciences, 83(11):1558–1564 (1994).

Yao, T., et al., "Inhibition of carbon tetrachloride–induced liver injury by liposomes containing vitamin E", Am Physiological Soc. G476–484 (1994).

* cited by examiner

EMULSION VEHICLE FOR POORLY SOLUBLE DRUGS

RELATED APPLICATIONS

This application is a continuation-in-part application of U.S. application number 09/003,173 filed Jan. 5, 1998 which claims the benefit under 35 U.S.C. §119(e) of U.S. provisional application No. 60/048,840 filed Jun. 6, 1997 and U.S. provisional application No. 60/034,188, filed Jan. 7, 1997.

FIELD OF THE INVENTION

This invention is in the field of pharmaceutical agents. In particular, this invention relates to pharmaceutical agents wherein tocopherol is used as a primary solvent.

BACKGROUND OF THE INVENTION

Hundreds of medically useful compounds are discovered each year, but clinical use of these drugs is possible only if a drug delivery vehicle is developed to transport them to their therapeutic target in the human body. This problem is particularly critical for drugs requiring intravenous injection in order to reach their therapeutic target or dosage but which are water insoluble or poorly water soluble. For such hydrophobic compounds, direct injection may be impossible or highly dangerous, and can result in hemolysis, phlebitis, hypersensitivity, organ failure and/or death. Such compounds are termed by pharmacists "lipophilic", "hydrophobic", or in their most difficult form, "amphiphobic".

A few examples of therapeutic substances in these categories are ibuprofen, diazepam, griseofulvin, cyclosporin, cortisone, proleukin, etoposide and paclitaxel. Kagkadis, KA et al. (1996) PDA J Pharm Sci Tech 50(5):317–323; Dardel, O. 1976. Anaesth Scand 20:221–24. Sweetana, S and MJU Akers. (1996) PDA J Pharm Sci Tech 50(5):330–342.

Administration of chemotherapeutic or anti-cancer agents is particularly problematic. The majority of these agents are poorly soluble and thus are difficult to deliver in aqueous solvents and supply at therapeutically useful levels. On the other hand, water-soluble anti-cancer agents are generally taken up by both cancer and non-cancer cells thereby exhibiting non-specificity.

Efforts to improve water-solubility and comfort of administration of such agents have not solved, and may have worsened, the two fundamental problems of cancer chemotherapy: 1) non-specific toxicity and 2) rapid clearance form the bloodstream by non-specific mechanisms. In the case of cytotoxins, which form the majority of currently available chemotherapies, these two problems are clearly related. Whenever the therapeutic is taken up by non-cancerous cells, a diminished amount of the drug remains available to treat the cancer, and more importantly, the normal cell ingesting the drug is killed.

To be effective in treating cancer, the chemotherapeutic must be present throughout the affected tissue(s) at high concentration for a sustained period of time so that it may be taken up by the cancer cells, but not at so high a concentration that normal cells are injured beyond repair. Obviously, water soluble molecules can be administered in this way, but only by slow, continuous infusion and monitoring, aspects which entail great difficulty, expense and inconvenience.

A more effective method of administering a cancer therapeutic, particularly a cytotoxin, is in the form of a dispersion of oil in which the drug is dissolved. These oily particles are made electrically neutral and coated in such a way that they do not interact with plasma proteins and are not trapped by the reticuloendothelial system (RES), instead remaining intact in the tissue or blood for hours, days or even weeks. It is desirable when the particles also distribute themselves into the surrounding lymph nodes which are injected at the site of a cancer. Nakamoto, Y et al. (1975) Chem Pharm Bull 23(10):2232–2238. Takahashi, T et al. (1977) Tohoku J Exp Med 123:235–246. In many cases direct injection into blood is the route of choice for administration. Even more preferable, following intravenous injection, the blood-borne particles may be preferentially captured and ingested by the cancer cells themselves. An added advantage of a particulate emulsion for the delivery of a chemotherapeutic is the widespread property of surfactants used in emulsions to overcome multidrug resistance.

For drugs that cannot be formulated as an aqueous solution, emulsions have typically been most cost-effective and gentle to administer, although there have been serious problems with making them sterile and endotoxin free so that they may be administered by intravenous injection. The oils typically used for pharmaceutical emulsions include saponifiable oils from the family of triglycerides, for example, soybean oil, sesame seed oil, cottonseed oil, safflower oil and the like. Hansrani, PK et al., (1983) J. Parenter Sci. Technol 37:145–150. One or more surfactants are used to stabilize the emulsion, and excipients are added to render the emulsion more biocompatible, stable and less toxic. Lecithin from egg yolks or soybeans is a commonly used surfactant. Sterile manufacturing can be accomplished by absolute sterilization of all the components before manufacture, followed by absolutely aseptic technique in all stages of manufacture. However, improved ease of manufacture and assurance of sterility is obtained by terminal sterilization following sanitary manufacture, either by heat or by filtration. Unfortunately, not all emulsions are suitable for heat or filtration treatments.

Stability has been shown to be influenced by the size and homogeneity of the emulsion. The preferred emulsion consists of a suspension of sub-micron particles, with a mean droplet diameter of no greater than 200 nanometers. A stable dispersion in this size range is not easily achieved, but has the benefit that it is expected to circulate longer in the bloodstream. Further, less of the stable dispersion in this size range is phagocytized non-specifically by the reticuloendothelial system. As a result the drug is more likely to reach its therapeutic target. Thus, a preferred drug emulsion will be designed to be actively taken up by the target cell or organ, and is targeted away from the RES.

The use of vitamin E in emulsions is known. In addition to the hundreds of examples where vitamin E in small quantities (for example, less than 1%, Lyons, R. T., Pharm Res 13(9): S-226, (1996) "Formulation development of an injectable oil-in-water emulsion containing the lipophilic antioxidants α-tocopherol and β-carotene") is used as an anti-oxidant in emulsions, the first primitive, injectable vitamin E emulsions per se were made by Hidiroglou for dietary supplementation in sheep and for research on the pharmacokinetics of vitamin E and its derivatives. Hidiroglou M. and Karpinski K. (1988) Brit J Nutrit 59:509–518.

For mice, an injectable form of vitamin E was prepared by Kato and coworkers. Kato Y., et al. (1993) Chem Pharm Bull 41(3):599–604. Micellar solutions were formulated with Tween 80, Brij 58 and HCO-60. Isopropanol was used as a co-solvent, and was then removed by vacuum evaporation; the residual oil glass was then taken up in water with vortexing as a micellar suspension. An emulsion was also prepared by dissolving vitamin E with soy phosphatidycholine (lecithin) and soybean oil. Water was added and the emulsion prepared with sonication.

In 1983, E-Ferol, a vitamin E emulsion was introduced for vitamin E supplementation and therapy in neonates. Alade S.L. et al. (1986) Pediatrics 77(4):593–597. Within a few months over 30 babies had died as a result of receiving the product, and the product was promptly withdrawn by FDA order. The surfactant mixture used in E-Ferol to emulsify 25 mg/mL vitamin E consisted of 9% Tween 80 and 1% Tween 20. These surfactants at the employed levels seem ultimately to have been responsible for the unfortunate deaths. This experience illustrates the need for improved formulations and the importance of selecting suitable biocompatible surfactants and carefully monitoring their levels in parenteral emulsions.

An alternative means of solubilizing low solubility compounds is direct solubilization in a non-aqueous milieu, for example alcohol (such as ethanol) dimethylsulfoxide or triacetin. An example in PCT application WO 95/11039 describes the use of vitamin E and the vitamin E derivative TPGS in combination with ethanol and the immunosuppressant molecule cyclosporin. U.S. Pat. No. 5,689,846 discloses various alcohol solutions of paclitaxel. U.S. Pat. No. 5,573,781 discloses the dissolution of paclitaxel in ethanol, butanol and hexanol and an increase in the antitumor activity of paclitaxel when delivered in butanol and hexanol as compared to ethanol. Alcohol-containing solutions can be administered with care, but are typically given by intravenous drip to avoid the pain, vascular irritation and toxicity associated with bolus injection of these solutions.

PCT publication WO 95/21217 (Dumex Ltd) discloses that tocopherols can be used as solvents and/or emulsifiers of drigs that are substantially insoluble in water, in particular for the preparation of topical formulations. The use of vitamin E-TPGS as an emulsifier in formulations containing high levels of α-tocopherol is mentioned in the specification (pages 7–8 and 12). Examples 1 to 5, disclosed formulations for topical administration comprising a lipid layer (α-tocopherol), the drug and Vitamin E-TPGS, in quantities of less than 25% w/w of the formulation, as an emulsifier. WO95/21217 does not suggest or describe anticancer agents or taxanes.

PCT Publication WO 97/03651 (Danbiosyst UK Ltd.) discloses lipid vehicle drug delivery compositions that contain at least five ingredients: a therapeutic drug, vitamin E, an oil in which the drug and vitamin E are dissolved, a stabilizer (either phospholipid, a lecithin, or a poloxamer which is a polyoxyethylene-polyoxypropylene copolymer) and water. The therapeutic drugs disclosed are itraconazole and paclitaxel. The "therapeutic emulsion" compositions require two oils in the dispersed phase where the therapeutic drug resides, vitamin E and another oil, typically a triglyceride such as soybean oil. The only working example with paclitaxel. Example 16, also contains both vitamin E and soybean oil.

N-methyl-2-pyrrolidone (NMP), under the trade name Pharmosolve™, can be used to improve the solubility of poorly soluble drugs in pharmaceutical formulations and has appeared in recent literature for use in veterinary medicine with forthcoming application in humans. Furthermore, polyvinylpyrrolidone (PVP) under the trade name Povidone™ with a molecular weight between 2,500 to 100,000 at a concentration of 1 to 5 percent (w/v) of the aqueous injectable base can be used as a co-solubilizer along with NMP.

U.S. Pat. No. 5,726,181 discloses antitumor compositions and suspensions comprising NMP and highly lipophilic camptothecin derivatives.

Polyethylene glycols (PEGs) and PVP are examples of two water-soluble polymers frequently used to modify the solubility behavior of drugs, including paclitaxel. Although the solubility of paclitaxel in both solvents is relatively high, in dilute aqueous solutions that are suitable for parenteral administration the solubility of the drug is low and the potential for drug precipitation upon dilution is high. In admixtures of PEG 400 and water containing 50–100% PEG 400, the solubility of paclitaxel varies from 0.2 to 175 mg/ml, respectively. Thus, paclitaxel solubilities are quite low where larger amounts of water are used, e.g., in 35% PEG 400 and 30% PVP in water are 0.03 mg/ml and ≦0.3 mg/ml, respectively. "Solubility of paclitaxel in Polyethylene Glycol 400/ Water Mixtures" (Straubinger, R. M. Biopharmacuitics of paclitaxel (Taxol); Formulation, activity and pharacokinetics, p.244 In Taxol, Science and Applications. (M. Suffness ed.), CRC Press, New York, 1995). The use of PEG-400 is not limited to paclitaxel and can be applied to other therapeutic agents which exhibit good solubility in polyethylene glycols (for example Etoposide). Derivative forms of paclitaxel including polyethylene glycol derivatives are described in U.S. Pat. No. 5,614,549.

In addition to poor solubility and the potential for drug precipitation with pharmaceutical formulations in non-aqueous solvents such as alcohol (ethanol, isopropanol, benzyl alcohol, etc.) along with surfactants another problem is the ability of these solvents to extract toxic substances, for example plasticizers, from their containers. The current commercial formulation for the anti-cancer drug paclitaxel, for example, consists of a mixture of hydroxylated castor oil and ethanol, and rapidly extracts plasticizers such as di-(2-ethylhexyl)-phthalate from commonly used intravenous infusion tubing and bags. Adverse reactions to the plasticizers have been reported, such as respiratory distress, necessitating the use of special infusion systems at extra expense and time. Waugh, et al. (1991) Am J. Hosp. Pharmacists 48:1520.

In light of these problems, it can be seen that the ideal emulsion vehicle would be inexpensive, non-irritating or even nutritive and palliative in itself, terminally sterilizable by either heat or filtration, stable for at least 1 year under controlled storage conditions, accommodate a wide variety of water insoluble and poorly soluble drugs and be substantially ethanol-free. In addition to those drugs which are lipophilic and dissolve in oils, also needed is a vehicle which will stabilize, and carry in the form of an emulsion, drugs which are poorly soluble in lipids and in water.

SUMMARY OF THE INVENTION

In order to meet these needs, the present-invention is directed to pharmaceutical compositions including: tocopherol, with and without an aqueous phase, a surfactant or mixtures of surfactants incorporating a co-solvent and a therapeutic agent. The compositions of the invention may be in the form of an emulsion, micellar solution or a self-emulsifying drug delivery system. The tocopherol molecule is preferably α-tocopherol. The compositions of the invention are generally substantially free of any monohydric alcohol.

The co-solvent may include water-soluble polymers, preferably polyethylene glycols or polyvinylpyrrolidone with or without N-methyl-2-pyrrolidone. Polyethylene glycols (PEGs) with a molecular weight between 100 to 10,000 are the most preferred co-solvent. Most preferred is PEG-400 in amounts greater than 1% by weight of the formulation.

The pharmaceutical compositions can be stabilized by the addition of various amphiphilic molecules, including anionic, nonionic, cationic, and zwitterionic surfactants. Preferably, these molecules are PEGylated surfactants and optimally PEGylated α-tocopherol.

The amphiphilic molecules further include surfactants such as ascorbyl-6 palmitate; stearylamine; sucrose fatty acid esters, pegylated phospholipids, various vitamin E derivatives and fluorine-containing surfactants (such as the Zonyl brand series) and a polyoxypropylene-polyoxyethylene glycol nonionic block copolymer.

The therapeutic agent of the emulsion may be a chemotherapeutic agent preferably a taxoid analog and most preferably, paclitaxel.

The emulsions of the invention can comprise an aqueous medium when in the form of an emulsion or micellar solution. This medium can contain various additives to assist in stabilizing the emulsion or in rendering the formulation biocompatible.

In one form, the invention is directed to a pharmaceutical composition comprising α-tocopherol, a chemotherapeutic selected from taxoids, taxins and taxanes, water and D-α-tocopherol polyethyleneglycol 1000 succinate. In another form, the invention is directed to a pharmaceutic composition comprising α-tocopherol, a co-solvent, one or more surfactants, an aqueous phase and a therapeutic agent wherein the composition is in the form of an emulsion or micellar solution and the solution is substantially free of any monohydric alcohol.

In a preferred format, the co-solvent may be polyethylene glycol, N-methyl-2-pyrrolidone, polyvinyl-pyrrolidone or mixtures thereof.

In a preferred format the surfactant is an α-tocopherol derivative and the polyethyleneglycol has a molecular weight between 100 to 10,000 most preferably from about 200 to about 1000.

In a preferred format the therapeutic agent is a chemotherapeutic agent selected from taxoids, taxines and taxanes.

The pharmaceutical compositions of the invention are typically formed by dissolving a therapeutic agent in the co-solvent to form a therapeutic agent solution; α-tocopherol is then added along with one or more surfactants to the therapeutic agent solution to form an oil solution of the therapeutic agent in the hydrophilic co-solvent. The oil solution is then blended with an aqueous phase to form a pre-emulsion. For IV delivery the pre-emulsion is further homogenized to form a fine emulsion. For oral delivery, the oil solution of the therapeutic agent in the co-solvent along with surfactants is typically encapsulated in a gelatin capsule.

In a preferred form of the method of the invention the therapeutic agent is dissolved in polyethylene glycol which allows the avoidance of the use of monohydric alcohols as a solvent.

BRIEF DESCRIPTION OF THE DRAWINGS

The invention will be better understood by reference to the figures, in which.

DETAILED DESCRIPTION OF THE INVENTION

Figure 1A:
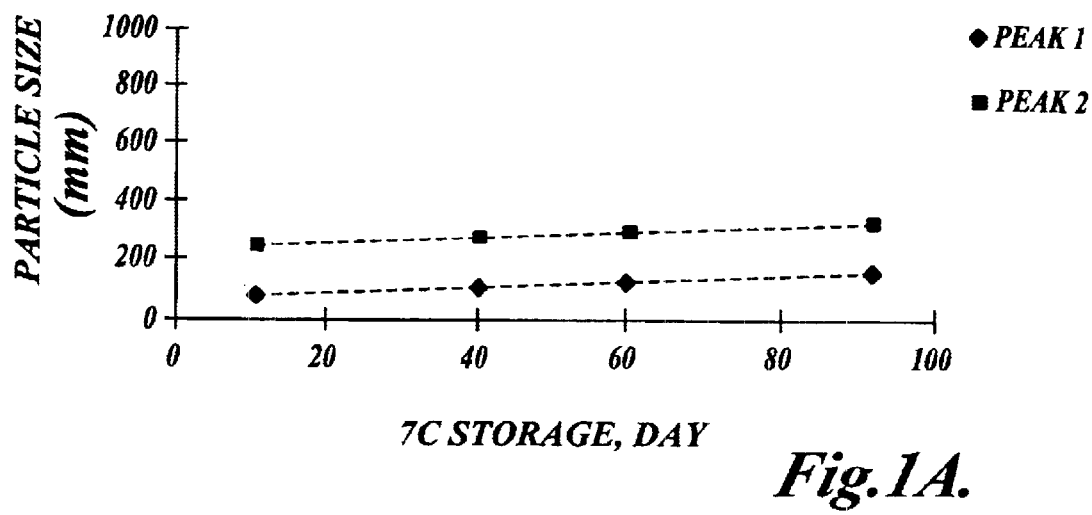
FIG. 1A shows the particle size of a paclitaxel emulsion (QWA) at 7° C. over time.

To ensure a complete understanding of the invention the following definitions are provided:

Tocopherols: tocopherols are a family of natural and synthetic compounds, also known by the generic names tocols or Vitamin E. α-tocopherol, is the most abundant and active form of this class of compounds and it has the following chemical structure (Scheme I):

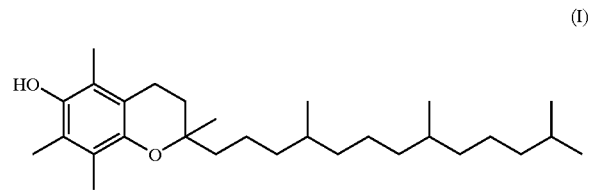

(I)

Other members of this class include α-, β-, γ-, and δ-tocotrienols, and α-tocopherol derivatives such as tocopherol acetate, phosphate, succinate, nitotinate and linoleate. In addition to their use as a primary solvent, tocopherols and their derivatives are useful as a therapeutic agents.

Surfactants: Surface active group of amphiphilic molecules which are manufactured by chemical processes or purified from natural sources or processes. These can be anionic, cationic, nonionic, and zwitterionic. Typical surfactants are described in Emulsions: Theory and Practice, Paul Becher, Robert E. Krieger Publishing, Malabar, Fla., 1965; Pharmaceutical Dosage Forms: Dispersed Systems Vol. I, Martin M. Rigear, Surfactants and U.S. Pat. No. 5,595,723 which is assigned to the assignee of this invention, Sonus Pharmaceuticals. All of these references are hereby incorporated by reference.

TPGS: TPGS or PEGylated vitamin E is a vitamin E derivative in which polyethylene glycol subunits are attached by a succinic acid diester at the ring hydroxyl of the vitamin E molecule. TPGS stands for D-α-tocopherol polyethyleneglycol 1000 succinate (MW=1513). TPGS is a non-ionic surfactant (HLB=16–18) with the structure of Scheme II:

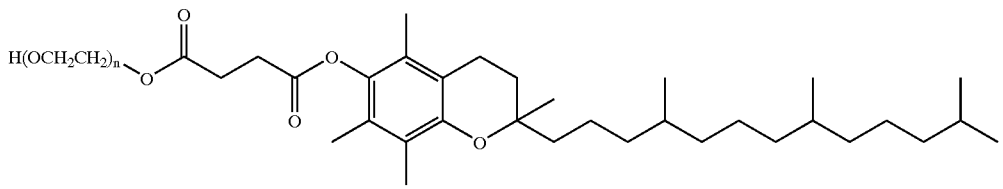

Various chemical derivatives of vitamin E TPGS including ester and ether linkages of various chemical moieties ate included within the definition of vitamin E TPGS.

Polyethylene glycol:Polyethylene glycol (PEG) is a hydrophilic, polymerized form of ethylene glycol, consisting of repeating units of the chemical structure—($CH_2$—$CH_2$—O—). The general formula for polyethylene glycol is $HOCH_2(CH_2OCH_2)_nCH_2OH$ or $H(OCH_2CH_2)_nOH$. The molecular weight ranges from 200 to 10,000. Such various forms are described as PEG-200, PEG-400 and the like.

N-Methyl-2-pyrrolidone: N-methyl-2-pyrrolidone (NMP) is an organic molecule with the following chemical structure:

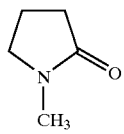

(III)

A GMP grade of this compound is available under the name Pharmasolve™ and is used to improve the solubility of poorly soluble drugs in pharmaceutical formulations. The enhanced solubility of certain drugs can be attributed to a complexing action with the nitrogen and carbonyl reactive centers of the molecule.

Polyvinyl pyrrolidone: Polyvinyl pyrrolidone (PVP) or Povidone is a water soluble polymer, consisting of repeatings units of the chemical structure:

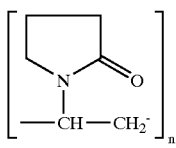

(IV)

It's average MW can vary between 2500 and $3\times10^6$ special grades of pyrogen free povidone are available for parenteral administration. Concentrations up to 5% w/v can be used as co-solvent for poorly soluble drugs.

Poloxamers or Pluronics: are synthetic block copolymers of ethylene oxide and propylene oxide having the general structure:

$OH(OCH_2CH_2)a\ (OCH_2CH_2CH_2)b\ (OCH2CH_2)a\ H$

The following variants based on the values of a and b are commercially available from BASF Performance Chemicals (Parsippany, N.J.) under the trade name Pluronic and which consist of the group of surfactants designated by the CTFA name of Poloxamer 108, 188, 217, 237, 238, 288, 338, 407, 101, 105, 122, 123, 124, 181, 182, 183, 184, 212, 231, 282, 331, 401, 402, 185, 215, 234, 235, 284, 333, 334, 335, and 403. For the most commonly used poloxamers 124, 188, 237, 338 and 407 the values of a and b are 12/20, 79/28, 64/37, 141/44 and 101/56, respectively.

Solutol HS-15: is a polyethylene glycol 660 hydroxystearate manufactured by BASF (Parsippany, N.J.). Apart from free polyethylene glycol and its monoesters, di-esters are also detectable. According to the manufacturer, a typical lot of Solutol HS-15 contains approximately 30% free polyethylene glycol and 70% polyethylene glycol esters.

Other surfactants: Other surfactants useful in the invention include ascorbyl-6 palmitate (Roche Vitamins, Nutley N.J.), stearylamine, and sucrose fatty acid esters (Mitsubishi Chemicals). Custom surfactants include those compounds with polar water-loving heads and hydrophobic tails, such as a vitamin E derivative comprising a peptide bonded polyglutamate attached to the ring hydroxyl and pegylated phytosterol. Other peptides may be bonded to vitamin E as well. Also, pegylated phospholipids are useful surfactants. Examples of pegylated phospholipids include PEG 2000 or PEG 5000 analogs of phosphatidylethanolamine where the fatty acyl chains contain $C_6$–$C_{24}$ fatty acids which can be saturated, unsaturated, mixtures thereof.

Hydrophile-lipophile balance: An empirical formula used to index surfactants. Its value varies from 1–45 and in the case of non-ionic surfactants from about 1–20. In general for lipophilic surfactants the HLB is less than 10 and for hydrophilic ones the HLB is greater than 10.

Biocompatible: Capable of performing functions within or upon a living organism in an acceptable manner, without undue toxicity or physiological or pharmacological effects.

Substantially free of any monohydric alcohol: A composition having a monohydric alcohol concentration less than about 1.0% (w/v) monohydric alcohol. As used herein, the term "monohydric" alcohol is an alcohol containing one hydroxyl group, such as but not limited to ethanol, butanol, isopropanol. The term "polyhydric" alcohol or "polyol" is an alcohol containing two or more hydroxyl groups, such as but not limited to, ethylene glycol, propylene glycol or polyethylene glycol (PEG). PEG is also referred to as polyglycol with ethylene glycol as a polymerized unit. Other suitable polyhydric alcohols for use herein include, but are not limited to, ethylene glycol (2-OH groups), glycerol (3-OH groups), sorbitol (6-OH groups) and mannitol (6-OH groups).

Emulsion: A colloidal dispersion of two immiscible liquids in the form of droplets, whose diameter, in general, are between 0.1 and 3.0 microns and which is typically optically opaque, unless the dispersed and continuous phases are refractive index matched. Such systems possess a finite stability, generally defined by the application or relevant reference system, which may be enhanced by the addition of amphiphilic molecules or viscosity enhancers.

Microemulsion: A thermodynamically stable isotropically clear dispersion of two immiscible liquids, such as oil and water, stabilized by an interfacial film of surfactant molecules. The microemulsion has a mean droplet diameter of less than 200 nm, in general between 10–50 nm. In the absence of water, mixtures of oil(s) and non-ionic surfactant (s) form clear and isotropic solutions that are known as self-emulsifying drug delivery systems (SEDDS) and have successfully been used to improve lipophilic drug dissolution and oral absorption.

Pegylated: Pegylated or ethoxylated means polyethylene glycol subunits attached to a given compound via a chemical linkage.

Aqueous Medium: A water-containing liquid which can contain pharmaceutically acceptable additives such as acidifying, alkalizing, buffering, chelating, complexing and solubilizing agents, antioxidants and antimicrobial preservatives, humectants, suspending and/or viscosity modifying agents, tonicity and wetting or other biocompatible materials.

Therapeutic Agent: Any compound natural of synthetic which has a biological activity, is soluble in the oil phase and has an octanol-buffer partition coefficient (Log P) of at least 2 to ensure that the therapeutic agent is preferentially dissolved in the oil phase rather than the aqueous phase. This includes peptides, non-peptides and nucleotides. Hydrophobic derivatives of water soluble molecules such as lipid conjugates/prodrugs are within the scope of therapeutic agent.

Chemotherapeutic: Any natural or synthetic molecule which is effective against one or more forms of cancer, and particularly those molecules which are slightly or completely lipophilic or which can be modified to be lipophilic. This definition includes molecules which by their mechanism of action are cytotoxic (anti-cancer agents), those which stimulate the immune system (immune stimulators) and modulators of angiogenesis. The outcome in either case is the slowing of the growth of cancer cells.

Chemotherapeutics include Taxol (paclitaxel) and related molecules collectively termed taxoids, taxines or taxanes. The structure of paclitaxel is shown in the figure below (Scheme V).

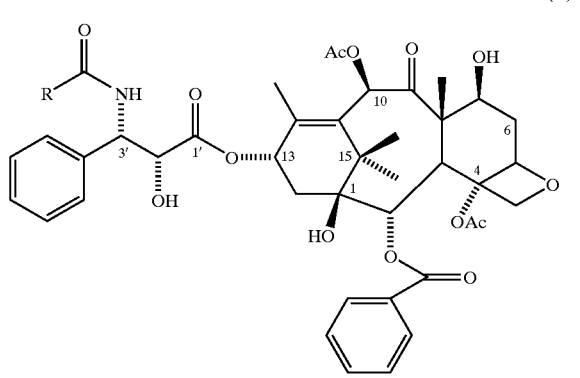

(V)

Included within the definition of "taxoids" are various modifications and attachments to the basic ring structure (taxoid nucleus) as may be shown to be efficacious for reducing cancer cell growth and to partition into the oil (lipid phase) and which can be constructed by organic chemical techniques known to those skilled in the art. These include but are not limited to benzoate derivatives of paclitaxel such as 2-debenzoyl-2-aroyl and C-2-acetoxy-C-4-benzoate paclitaxel, 7-deocytaxol, C-4 aziridine paclitaxel, as wells as various paclitaxel conjugates with natural and synthetic polymers, particularly with fatty acids, phospholipids, and glycerides and 1,2-diacyloxypropane-3-amine. Docetaxel (Taxotere) is also a preferred taxane. The structure of the taxoid nucleus is shown in Scheme VI.

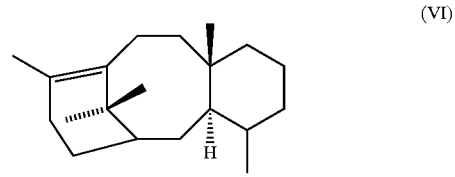

(VI)

Also included within the scope of the present invention are natural products that share structural similarities with paclitaxel i.e. they incorporate a common pharmacophore proposed for microtubule-stabilizing agents. These compounds include but not limited to epothilone A and B, discodermolide, nonataxel and eleutherobin (Chem. Eng. News 1999, 77 (17): 35–36)

Chemotherapeutics include podophyllotoxins and their derivatives and analogues. The core ring structure of these molecules is shown in the following figure (Scheme VII):

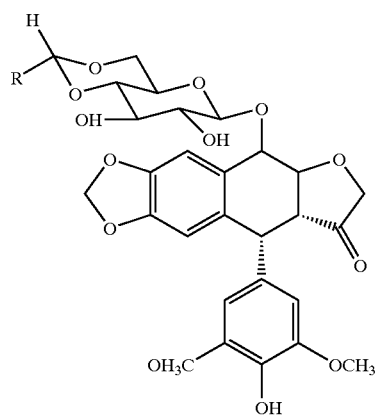

Another important class of chemotherapeutics useful in this invention are camptothecins, the basic ring structure of which is shown in the following figure, but includes any derivatives and modifications to this basic structure which retain efficacy and preserve the lipophilic character of the molecule shown below (Scheme VIII).

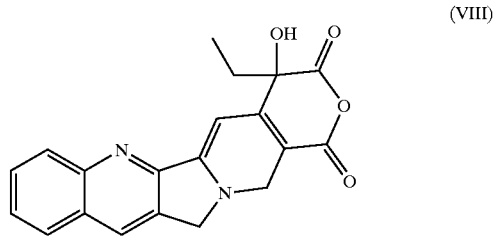

(VIII)

Another preferred class of chemotherapeutics useful in this invention are the figure (Scheme IX):

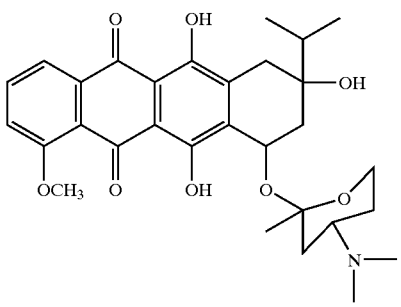

(IX)

Suitable lipophilic modifications of Scheme IX include substitutions at the ring hydroxyl group or sugar amino group.

Another important class of chemotherapeutics are compounds which are lipophilic or can be made lipophilic by molecular chemosynthetic modifications well known to those skilled in the art, for example by combinatorial chemistry and by molecular modelling, and are drawn from the following list: Taxotere, Amonafide, Illudin S, 6-hydroxymethylacylfulvene Bryostatin 1,26-succinylbryostatin 1, Palmitoyl Rhizoxin, DUP941, Mitomycin B, Mitomycin C, Penclomedine. Interferon α2b, angiogenesis inhibitor compounds, Cisplatin hydrophobic complexes such as 2-hydrazino-4,5-dihydro-1H-imidazole with platinum chloride and 5-hydrazino-3,4-dihydro-2H-pyrrole with platinum chloride, vitamin A, vitamin E and its derivatives, particularly tocopherol succinate.

Other compounds useful in the invention include: 1,3-bis (2-chloroethyl)-1-nitrosurea ("carmustine" or "BCNU"), 5-fluorouracil, doxorubicin ("adriamycin"), epirubicin, aclarubicin, Bisantrene (bis(2-imidazolen-2-ylhydrazone)-9, 10-anthracenedicarboxaldehyde, mitoxantrone, methotrexate, edatrexate, muramyl tripeptide, muramyl dipeptide, lipopolysaccharides, 9-b-d-arabinofuranosyladenine ("vidarabine") and its 2-fluoro derivative, resveratrol, retinoic acid and retinol, Carotenoids, and tamoxifen.

Other compounds useful in the application of this invention include: Decarbazine, Lonidamine, Piroxantrone, Anthrapyrazoles, Etoposide, Camptothecin, 9-aminocamptothecin, 9-nitrocamptothecin, camptothecin-11 ("Irinotecan"), Topotecan, Bleomycin, the Vinca alkaloids and their analogs [Vincristine, Vinorelbine, Vindesine, Vintripol, Vinxaltine, Ancitabine], 6-aminochrysene, and navelbine.

Other compounds useful in the application of the invention are mimetics of taxol, eleutherobins, sarcodictyins, discodermolides and epothiolones.

Other compounds useful in the invention are microtubule targeting agents. Microtubule targeting agents may bind to a protein called tubulin and thus prevent microtubule polymerization. Representative microtubule binding agents include epothilones, elutherobin and discodermolide.

Taking into account these definitions, the present invention is directed to pharmaceutical compositions in the form of emulsions, micellar solutions or self-emulsifying drug delivery systems which are substantially free of ethanol solvent.

The therapeutic agents of the compositions of this invention can initially be solubilized in a co-solvent. In the case of ethanol during the preparation of the oil phase the ethanol is removed and a substantially ethanol-free composition is formed. The ethanol concentration is less than 1% (w/v), preferably less than 0.5%, and most preferably less than 0.3%. The therapeutic agents can also be solubilized in methanol, propanol, chloroform, isopropanol, butanol and pentanol. These solvents are also removed prior to use.

In a preferred embodiment, the therapeutic agents of the compositions of the invention can initially be solubilized in non-volatile co-solvents such as dimethylsulfoxide (DMSO), dimethylamide (DMA), propylene glycol (PG), polyethylene glycol (PEG), N-methyl-2-pyrrolidone (NMP) and polyvinylpyrrolidone (PVP); NMP or a water-soluble polymer such as PEG or PVP (Table 1) are particularly preferred.

A major advantage/improvement of using PEG-400 to solubilize therapeutic agents rather than alcohols such as ethanol is that a volatile solvent does not have to be removed or diluted prior to administration of the therapeutic agent. The final polyethylene glycol levels in the emulsion can be varied from 1–50%, preferably from 1–25% and more preferably from 1–10% (w/w). Suitable polyethylene glycol solvents are those with an average molecular weight between 200 and 600 preferably between 300 and 400 (Table 1). In the case of self-emulsified systems for oral administration, high molecular weight PEGs (1,000–10,000) can also be included as solidification agents to form semi-solid formulations which can be filled into hard gelatin capsules.

TABLE 1

Physical Properties of Low Molecular Weight Polyethylene Glycols

| Physical Property | PEG 200 | PEG 300 | PEG 400 | PEG 600 |
|---|---|---|---|---|
| Molecular weight | 190–210 | 285–315 | 380–420 | 570–630 |
| Viscosity (mPas) | 46–53 | 66–74 | 85–95 | 130–150 |
| Refractive Index (25° C.) | 1.459 | 1.463 | 1.465 | 1.467 |
| Freezing point (° C.) | −50 | −16 to −12 | −3 to 8 | 15 to 25 |

Solubilization of the therapeutic agents of the invention in polyethylene glycol or other non-volatile co-solvents (PVP, NMP) avoids the necessity of solubilizing the therapeutic agents of the invention in monohydric alcohols such as ethanol or other volatile solvents. Use of polyethylene glycol or N-methyl-2-pyrrolidone eliminates the need to remove the solvent prior to use of the emulsions therapeutically.

The final polyethylene glycol levels in the emulsion can be varied from 1–50%, preferably from 1–25% and more preferably from 1–10% (w/w).

The compositions of the invention contain tocopherol as a carrier for therapeutic drugs, which can be administered to animals or humans via intravascular, oral, intramuscular, cutaneous and subcutaneous routes. Specifically, the emulsions can be given by any of the following routes, among others: intraabdominal, intraarterial, intraarticular, intracapsular, intracervical, intracranial, intraductal, intradural, intralesional, intralocular, intralumbar, intramural, intraocular, intraoperative, intraparietal, intraperitoneal, intrapleural, intrapulmonary, intraspinal, intrathoracic, intratracheal, intratympanic, intrauterine, and intraventricular. The emulsions of the present invention can be nebulized using suitable aerosol propellants which are known in the art for pulmonary delivery of lipophilic compounds.

In its first aspect, the invention is directed to the use of tocopherol as the hydrophobic dispersed phase of emulsions containing water insoluble, poorly water soluble therapeutic agents, water soluble ones which have been modified to be less water soluble or mixtures thereof. In a preferred embodiment α-tocopherol is employed. Also called vitamin E, α-tocopherol is not a typical lipid oil. It has a higher polarity than most lipid oils, particularly triglycerides, and is not saponifiable. It has practically no solubility in water.

In the second aspect, the invention is an tocopherol emulsion in the form of a self-emulsifying system where the system is to be used for the oral administration of water insoluble (or poorly water soluble or water soluble agents modified to be less water soluble or mixtures thereof) drugs where that is desired. In this embodiment, an oil phase with surfactant and drug or drug mixture is encapsulated into a soft or hard gelatin capsule. Suitable solidification agents with melting points in the range of 40 to 60° C. such as high molecular weight polyethylene glycols (MW>1000) and glycerides such as those available under the trade name Gelucire (Gattefose Corp. Saint Priest, France) can be added to allow filling of the formulation into a hard gelatin capsule at high temperature. Semi-solid formulations are formed upon room temperature equilibration. Upon dissolution of the gelatin in the stomach and duodenum, the oil is released and forms a fine emulsion with a mean droplet diameter of between 2–5 microns spontaneously. The emulsion is then taken up by the microvilli of the intestine and released into the bloodstream.

In a third aspect, the invention comprises microemulsions containing tocopherol preferably α-tocopherol Microemulsions refer to a sub-class of emulsions where the emulsion suspension is essentially clear and indefinitely stable by virtue of the extremely small size of the oil/drug microaggregates dispersed therein.

In a fourth aspect of the invention, PEGylated vitamin E (TPGS) is used as a primary surfactant in emulsions of vitamin E. PEGylated vitamin E is utilized as a primary surfactant, a stabilizer and also as a supplementary solvent in emulsions of vitamin E. Polyethylene glycol (PEG) is also useful as a co-solvent in the emulsions of this invention. Of particular use is polyethylene glycol 200, 300, 400 or mixtures thereof.

The α-tocopherol concentration of the emulsions of this invention can be from about 1 to about 10% w/v. The ratio of α-tocopherol to TPGS is optimally from about 1:1 to about 10:1 (w/w).

The emulsions of the invention may further include surfactants such as ascorbyl-6 palmitate; stearylamine; pegylated phospholipids, sucrose fatty acid esters and various vitamin E derivatives comprising α-tocopherol nicotinate, tocopherol phosphate, and nonionic, synthetic surfactant mixtures, such as polyoxypropylene-polyoxyethylene glycol nonionic block copolymer.

The emulsions of the invention can comprise an aqueous medium. The aqueous phase generally has an osmolality of approximately 300 mOsm and may include sodium chloride, sorbitol, mannitol, polyethylene glycol, propylene glycol albumin, polypep and mixtures thereof. This medium can also contain various additives to assist in stabilizing the emulsion or in rendering the formulation biocompatible. Acceptable additives include acidifying agents, alkalizing agents, antimicrobial preservatives, antioxidants, buffering agents, chelating agents, suspending and/or viscosity-increasing agents, and tonicity agents. Preferably, agents to control the pH, tonicity, and increase viscosity are included. Optimally, a tonicity of at least 250 mOsm is achieved with an agent which also increases viscosity, such as sorbitol or sucrose.

The emulsions of the invention for intravenous injection have a particle size (mean droplet diameter) of 10 to 500 nm, preferably 10 to 200 nm and most preferably 10 to 100 nm. For intravenous emulsions, the spleen and liver will eliminate particles greater than 500 mn in size through the RES.

A preferred form of the invention includes paclitaxel, a very water-insoluble cytotoxin used in the treatment of uterine cancer and other carcinomas. An emulsion composition of the present invention comprises a solution of vitamin E containing paclitaxel at a concentration of up to 20 mg/mL, four times that currently available by prescription, and a biocompatible surfactant such that the emulsion microdroplets are less than 0.2 microns and are terminally sterilizable by filtration.

Preferred injectable compositions contain: 0.1–1.0% paclitaxel (1–10 mg/ml); 1–10% PEG400; 3–10% Vitamin E; 1–6% TPGS and 0.5–2.5% Pluronic F127.

Another preferred composition contains: 1.0 paclitaxel (10 mg/mi), 6% PEG400, 8% Vitamin E, 5% TPGS, 1% Pluronic F127 and 80% aqueous solution.

Preferred formulations for self-emulsifying systems are as follows: 0.1–20% paclitaxel, 10–90% Vitamin E, 10–90% PEG 400 or N-methyl-2-pyrrolidone, 5–50% TPGS, 5–50% a secondary hydrophilific surfactant, such as Polysorbates (Tween 80), Pluronics (Pluronic F127) or Cremophor EL/RH40, Solutol HS-15). The oil phase (vitamin E) can optionally contain polyvinylpyrrolidone, glycerol and propylene glycol esters such as mono-/di-/triglycerides and mono-diesters of propylene glycol. In addition, high MW PEGs (1,000–10,000) and high melting point glycerol esters can be included to provide the formulation with semisolid consistency.

A further embodiment of the invention is a method of treating carcinomas comprising the parenteral administration of a bolus dose of paclitaxel in vitamin E emulsion with and without PEGylated vitamin E by intravenous injection once daily or every second day over a therapeutic course of several weeks. Such method can be used for the treatment of carcinomas of the breast, lung, skin and uterus.

The general principles of the present invention may be more fully appreciated by reference to the following non-limiting examples.

EXAMPLES

Example 1

Dissolution of Paclitaxel in α-tocopherol

α-Tocopherol was obtained from Sigma Chemical Company (St Louis Mo.) in the form of a synthetic dl-α-tocopherol of 95% purity prepared from phytol. The oil was amber in color and very viscous. Paclitaxel was purchased from Hauser Chemical Research (Boulder Colo.), and was 99.9% purity by HPLC. Paclitaxel 200 mg was dissolved in 6 mL of dry absolute ethanol (Spectrum Chemical Manufacturing Corp, Gardenia Calif.) and added to 1 gm α-tocopherol. The ethanol was then removed by vacuum at 42OC until the residue was brought to constant weight. Independent studies showed that the ethanol content was less than 0.3% (w/v).

The resultant solution was clear, amber and very viscous, with a nominal concentration of 200 mg/gm (w/w) paclitaxel in α-tocopherol. Higher concentrations of paclitaxel (up to 400 mg/gm, w/w) can be solubilized in α-tocopherol.

Example 2

Anionic Surfactant Used to Prepare α-tocopherol Emulsions

Paclitaxel 2 gm in 10 gm of α-tocopherol, prepared as described in Example 1, was emulsified with ascorbyl palmitate as the triethanolamine salt by the following method. A solution consisting of ascorbic acid 20 mM was buffered to pH 6.8 with triethanolamine as the free base to form 2× buffer. 50 mL of the 2× buffer was placed in a Waring blender. 0.5 gm of ascorbyl-6-palmitate (Roche Vitamins and Fine Chemicals, Nutley N.J.), an anionic surfactant, was added and the solution blended at high speed for 2 min at 40° C. under argon. The α-tocopherol containing paclitaxel was then added into the blender with the surfactant and buffer. Mixing was continued under argon until a coarse, milky, pre-emulsion was obtained, approximately after 1 min at 40° C. Water for injection was then added, bringing the final volume to 100 mL.

The pre-emulsion was transferred to the feed vessel of a Microfluidizer Model 110Y (Microfluidics Inc, Newton Mass.). The unit was immersed in a bath to maintain a process temperature of approximately 60° C. during homogenization, and was flushed with argon before use. After priming, the emulsion was passed through the homogenizer in continuous re-cycle for 10 minutes at a pressure gradient of about 18 kpsi across the interaction head. The flow rate was about 300 mL/min, indicating that about 25 passes through the homogenizer resulted.

The resultant paclitaxel emulsion in an α-tocopherol vehicle was bottled in amber vials under argon and stored with refrigeration at 7° C. and 25° C. Samples were taken at discrete time intervals for particle sizing and chemical analysis.

Data taken with a Nicomp Model 370 Submicron Particle Sizer (Particle Sizing Systems Inc, Santa Barbara Calif.) showed that the emulsion had a mean particle diameter of 280 nm.

Example 3

Use of PEGylated Vitamin E (TPGS)

A ternary phase diagram was constructed for α-tocopherol, PEGylated vitamin E (TPGS, vitamin-E polyoxyethyleneglycol-1000-succinate, obtained from Eastman Chemical Co., Kingsport Tenn.), and water. TPGS was first melted at 42° C. and mixed gravimetrically with α-tocopherol at various proportions from 1 to 100% TPGS, the balance being α-tocopherol. Mixtures were miscible at all concentrations. Water was then added to each mixture in such a way that the final water concentration was increased stepwise from zero to 97.5%. At each step, observations were made of the phase behavior of the mixture. As appropriate, mixing was performed by vortexing and sonication, and the mixture was heated or centrifuged to assess its phase composition.

A broad area of biphasic o/w emulsions suitable for parenteral administration was found at water concentrations above 80%. The emulsions formed were milky white, free flowing liquids that contained disperse α-tocopherol microparticles stabilized by non-ionic surfactant. Also in this area, microemulsions potentially suitable as drug carriers were observed at TPGS to oil ratios above about 1:1. At lower water content, a broad area containing transparent gels (reverse emulsions) was noted. Separating the two areas (high and low water content) is an area composed of opaque, soap-like liquid crystals.

Phase diagrams of α-tocopherol with surfactant combinations, for example TPGS with a nonionic, anionic or cationic co-surfactant (for example glutamyl stearate, ascorbyl palmitate or Pluronic F-68), or drug can be prepared in a similar manner.

Example 4

α-Tocopherol Emulsion for Intravenous Delivery of Paclitaxel

A formulation of the following composition was prepared:

| | |
|---|---|
| paclitaxel | 1.0 gm % |
| α-tocopherol | 3.0 gm % |
| TPGS | 2.0 gm % |
| Ascorbyl-6-Palmitate | 0.25 gm % |
| Sorbitol | 5.0 gm % |
| Triethanolamine | to pH 6.8 |
| Water | qs to 100 mL |

The method of preparation was as follows: synthetic α-tocopherol (Roche Vitamins, Nutley N.J.), paclitaxel (Hauser, Boulder Colo.), ascorbyl 6-palmitate (Aldrich Chemical Co, Milwaukee Wis.) and TPGS were dissolved in 10 volumes of anhydrous undenatured, ethanol (Spectrum Quality Products, Gardenia Calif.) with heating to 40–45° C. The ethanol was then drawn off with vacuum until no more than 0.3% remained by weight.

Pre-warmed aqueous solution containing a biocompatible osmolyte and buffer were added with gentle mixing and a white milk formed immediately. This mixture was further improved by gentle rotation for 10 minutes with continuous warming at 40–45° C. This pre-mixture at about pH 7 was then further emulsified as described below.

The pre-mixture at 40–45° C. was homogenized in an Avestin Chomogenizer (Avestin, Ottawa Canada) at 26 Kpsi for 12 minutes at 44° C. The resultant mixture contained microparticles of α-tocopherol with a mean size of about 200 nm. Further pH adjustment was made with an alkaline 1 M solution of triethanolamine (Spectrum Quality Products).

In order to avoid gelation of the TPGS during the early stage of emulsification, all operations were performed above 40° C. and care was taken to avoid exposure of the solutions to cold air by covering all vessels containing the mixture. Secondly, less than 2% TPGS should generally be dissolved in α-tocopherol oil before pre-emulsification, the balance of the TPGS being first dissolved in the aqueous buffer before the pre-emulsion is prepared. The solution gels at concentrations of TPGS higher than 2%.

Figure 1B:
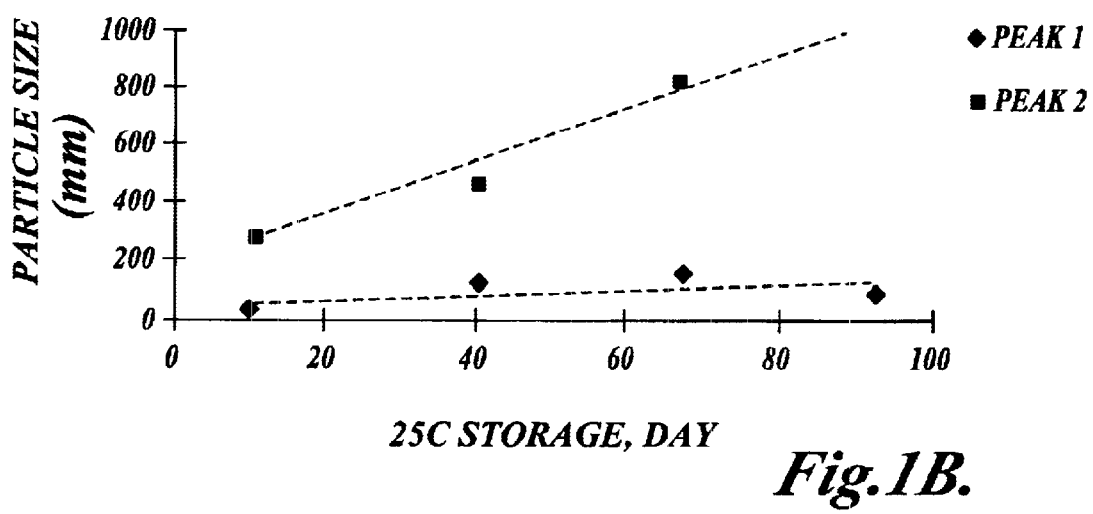
FIG. 1B shows the particle size of a paclitaxel emulsion (QWA) at 25° C. over time.

Physical stability of the emulsion was then examined by placing multiple vials on storage at 4° C. and 25° C. Over several months, vials were periodically withdrawn for particle sizing. Mean particle size, as determined with the Nicomp Model 370 (Particle Sizing Systems, Santa Barbara Calif.), is shown for the two storage temperatures in FIG. 1. The particle size distribution was bi-modal.

Example 5

Chemical Stability of Paclitaxel in an α-tocopherol Emulsion

Figure 2:
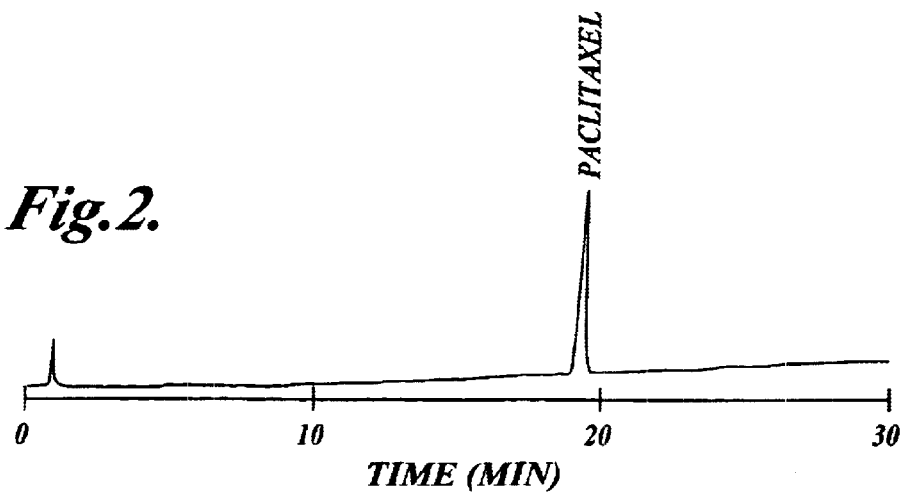
FIG. 2 is an HPLC chromatogram showing the integrity of a paclitaxel in an emulsion as described in Example 5.

After emulsification, the formulation of Example 4 was analyzed for paclitaxel on a Phenosphere CN column (5 microns, 150×4.6 mm). The mobile phase consisted of a methanol/water gradient, with a flow rate of 1.0 mL/min. A UV detector set at 230 nm was used to detect and quantitate paclitaxel. A single peak was detected (FIG. 2), which had a retention time and mass spectrogram consistent with native reference paclitaxel obtained from Hauser Chemical (Boulder Colo.).

Figure 3A:
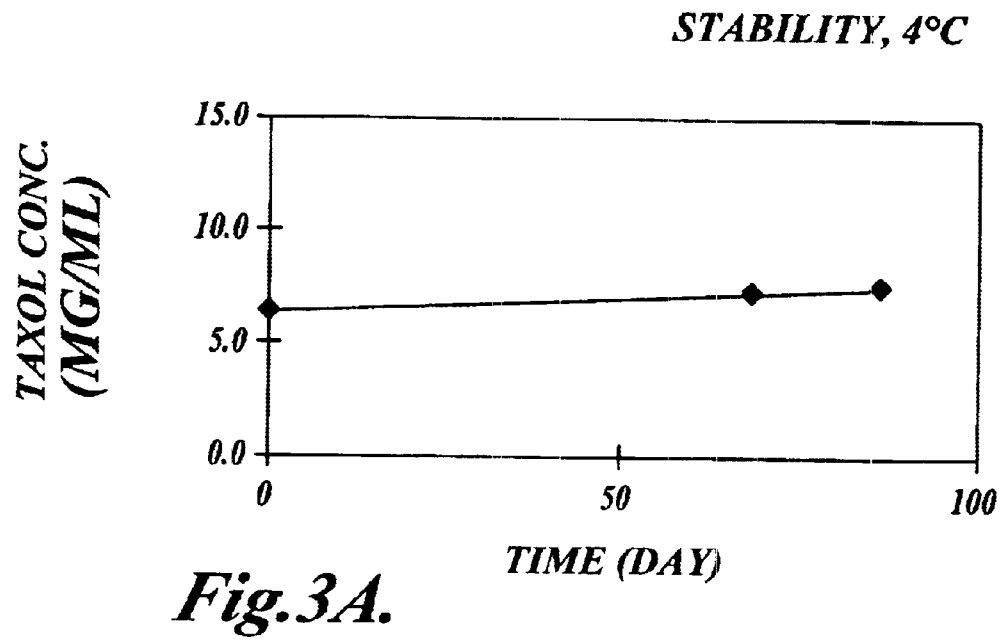
FIG. 3A shows the paclitaxel concentration of a paclitaxel emulsion (QWA) at 4° C. over time.
Figure 3B:
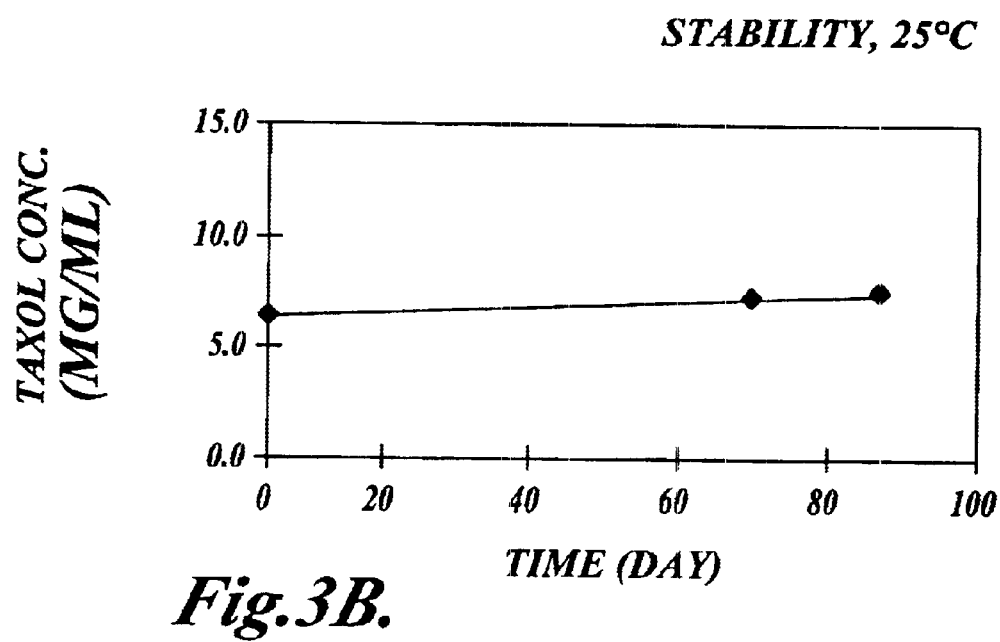
FIG. 3B shows the paclitaxel concentration of a paclitaxel emulsion (QWA) at 25° C. over time.

Chemical stability of the emulsion of example 4 was examined by HPLC during storage. The data of FIG. 3 demonstrate that paclitaxel remains stable in the emulsion for periods of at least 3 months, independent of the storage temperature. Taken together, the data of FIGS. 2 and 3 demonstrate successful retention of drug potency and emulsion stability when stored at 4° C. for a period of at least 3 months.

Example 6
Paclitaxel Emulsion Formulation QWA
An emulsion of paclitaxel 10 mg/ml for intravenous drug delivery, having the following composition, was prepared as described in Example 4.

| | |
|---|---|
| paclitaxel | 1.0 gm % |
| α-tocopherol | 3.0 gm % |
| TPGS | 1.5 gm % |
| Ascorbyl-6-Palmitate | 0.25 gm % |
| Sorbitol | 4.0 gm % |
| Triethanolamine | to pH 6.8 |
| Water | qs to 100 mL |

Example 7
Paclitaxel Emulsion Formulation QWB
A second emulsion of paclitaxel 10 mg/ml for intravenous drug delivery, having the following composition, was prepared as described in Example 4.

| | |
|---|---|
| paclitaxel | 1.0 gm % |
| α-tocopherol | 3.0 gm % |
| TPGS | 1.5 gm % |
| Solutol HS-15 | 1.0 gm % |
| Sorbitol | 4.0 gm % |
| Triethanolamine | to pH 6.8 |
| Water | qs to 100 mL |

Solutol HS-15 is a product of BASF Corp, Mount Olive NJ.

Example 8
10 mg/mL Paclitaxel Emulsion Formulation QWC
A third emulsion formulation of paclitaxel 10 mg/ml was prepared as follows using Poloxamer 407 (BASF Corp, Parsippany N.J.) as a co-surfactant.

| | |
|---|---|
| paclitaxel | 1.0 gm % |
| α-tocopherol | 6.0 gm % |
| TPGS | 3.0 gm % |
| Poloxamer 407 | 1.0 gm % |
| Sorbitol | 4.0 gm % |
| Triethanolamine | to pH 6.8 |
| Water for injection | qs to 100 mL |

In this example, 1.0 gm Poloxamer 407 and 1.0 gm paclitaxel were dissolved in 6.0 gm α-tocopherol with ethanol 10 volumes and gentle heating. The ethanol was then removed under vacuum. Separately, an aqueous buffer was prepared by dissolving 3.0 gm TPGS and 4.0 gm sorbitol in a final volume of 90 mL water for injection. Both oil and water solutions were warmed to 45° C. and mixed with sonication to make a pre-emulsion. A vacuum was used to remove excess air from the pre-emulsion before homogenization.

Homogenization was performed in an Avestin C5 as already described. The pressure differential across the homogenization valve was 25 kpsi and the temperature of the feed was 42°–45° C. A chiller was used to ensure that the product exiting the homogenizer did not exceed a temperature of 50° C. Flow rates of 50 mL/min were obtained during homogenization. After about 20 passes in a recycling mode, the emulsion became more translucent. Homogenization was continued for 20 min. Samples were collected and sealed in vials as described before. A fine α-tocopherol emulsion for intravenous delivery of paclitaxel was obtained. The mean particle diameter of the emulsion was 77 nm. Following 0.22μ sterile filtration through a 0.22 micron Durapore filter (Millipore Corp, Bedford Mass.), the emulsion was filled in vials and stored at 4° C. until used for intravenous injection.

Example 9
5 mg/mL Paclitaxel Emulsion Formulation QWC
An additional emulsion of paclitaxel was prepared as described in Example 8 but incorporating 5 instead of 10 mg/ml of the drug. The composition of this emulsion is as follows:

| | |
|---|---|
| paclitaxel | 0.5 gm % |
| α-tocopherol | 6.6 gm % |
| TPGS | 3.0 gm % |
| Poloxamer 407 | 1.0 gm % |
| Sorbitol | 4.0 gm % |
| Triethanolamine | to pH 6.8 |
| Water for injection | qs to 100 mL |

Following homogenization as described in example 8, a somewhat translucent emulsion of α-tocopherol and paclitaxel with a mean particle diameter of 52 nm was obtained. Following sterile filtration through a 0.22 micron Durapore filter (Millipore Corp, Bedford Mass.), the emulsion was filled in vials and stored at 4° C. until used for intravenous injection. Drug losses on filtration were less than 1%.

Example 10
Paclitaxel Emulsion Formulation QWD
A fifth emulsion of α-tocopherol for intravenous administration of paclitaxel was prepared as follows:

| | |
|---|---|
| paclitaxel | 0.5 gm % |
| α-tocopherol | 6.0 gm % |
| TPGS | 3.0 gm % |
| Poloxamer 407 | 1.5 gm % |
| Polyethyleneglycol 200 | 0.7 gm % |
| Sorbitol | 4.0 gm % |
| Triethanolamine | to pH 6.8 |
| Water for injection | qs to 100 mL |

Synthetic α-tocopherol USP-FCC obtained from Roche Vitamins (Nutley, N.J.) was used in this formation. Polyethyleneglycol 200 (PEG-200) was obtained from Sigma Chemical Co.

Following homogenization, a somewhat translucent emulsion with a mean particle diameter of 60 nm was obtained. Following 0.22μ sterile filtration through a 0.22 micron Durapore filter (Millipore Corp, Bedford Mass.), the emulsion was filled in vials and stored at 4° C. until used for intravenous injection. Drug losses on filtration were less than 1%.

Example 11
Dissolution of Paclitaxel in TPGS and Preparation of Micellar Solutions.
We observed good solubility of paclitaxel in TPGS, about 100 mg drug per 1.0 gm of TPGS. Micellar solutions of TPGS containing paclitaxel were prepared as follows. A stock solution of paclitaxel in TPGS was made up by dissolving 90 mg paclitaxel in 1.0 gm TPGS at 45° C. with ethanol, which was then removed under vacuum. Serial dilutions were then prepared by diluting the paclitaxel stock with additional TPGS to obtain paclitaxel in TPGS at concentrations of 0.1, 1, 5, 10, 25, 50, 75 and 90 mg/mL. Using fresh test tubes, 100 mg of each paclitaxel concentration in TPGS was dissolved in 0.9 mL water. All test tubes were mixed by vortex and by sonication at 45° C. Clear micellar solutions in water were obtained corresponding to final paclitaxel concentrations of 0.01, 0.1, 0.5, 1.0, 2.5, 5.0, 7.5 and 9.0 mg/mL.

A Nicomp Model 370 laser-particle sizer (Particle Sizing Systems, Santa Barbara Calif.) was used to examine the solutions. Particle sizes on the order of 10 nm were obtained, consistent with the presence of micelles of TPGS and paclitaxel.

Micellar solutions of paclitaxel in TPGS containing up to 2.5 mg/mL paclitaxel were stable for at least 24 hr whereas those at 5.0, 7.5 and 9.0 mg/mL were unstable and drug crystals formed rapidly and irreversibly. These observations imply that paclitaxel remains solubilized only in the presence of an α-tocopherol-rich domain within the emulsion particles. Thus, an optimum ratio of α-tocopherol to TPGS is needed in order to produce emulsions in which higher concentrations of paclitaxel can be stabilized.

When adjusted to the proper tonicity and pH, micellar solutions have utility for slow IV drip administration of paclitaxel to cancer patients, although the AUC is expected to be low.

The utility of TPGS in α-tocopherol emulsions is a synergy of several desirable characteristics. First, it has its own affinity for paclitaxel, probably by virtue of the α-tocopherol that makes up the hydrophobic portion of its molecular structure. Secondly, interfacial tension of TPGS in water with α-tocopherol is about 10 dynes/cm, sufficient to emulsify free α-tocopherol, especially when used with a co-surfactant. Third, polyoxyethylated surfactants such as TPGS, have well established, superior properties as a "stealth coat" for injectable particles, by dramatically reducing trapping of the particles in the liver and spleen, as is well known in the art. But the unexpected and unique finding with TPGS as a surfactant for α-tocopherol emulsions, was the finding of all three desirable characteristics in a single molecule. An additional advantage of TPGS is the fact that it forms stable self-emulsifying systems in mixtures with oils and solvents such as propylene glycol and polyethylene glycol, suggesting a synergy when used with α-tocopherol for oral drug delivery.

When adjusted to the proper tonicity and pH, micellar solutions have utility for slow IV drip administration of paclitaxel to cancer patients, although the AUC is expected to be low.

Example 12
20 mg/mL Paclitaxel Emulsion Formulation

A coarse, emulsion containing 20 mg/mL paclitaxel in α-tocopherol was obtained with 5% α-tocopherol and 5% TPGS by the methods described in Example 4, simply by increasing the concentrations. No effort was made to test higher concentrations simply because no further increase is necessary for clinically useful intravenous emulsions.

Example 13
Use of Other PEG Surfactants in α-tocopherol Emulsions

A variety of other pegylated surfactants, for example Triton X-100, PEG 25 propylene glycol stearate, Brij 35 (Sigma Chemical Co), Myrj 45, 52 and 100, Tween 80 (Spectrum Quality Products), PEG 25 glyceryl trioleate (Goldschmidt Chemical Corp, Hopewell Va.), have utility in emulsifying α-tocopherol.

However, experiments with some other pegylated surfactants failed to convincingly stabilize paclitaxel in an α-tocopherol emulsion. To demonstrate the unique utility of TPGS, three emulsions were prepared as described in Example 9, but Tween 80 and Myrj 52 were substituted for TPGS as the primary surfactant in separate emulsions. These two surfactants were chosen because Tween 80 and Myrj 52 have HLB values essentially equivalent to TPGS and make-reasonably good emulsions of α-tocopherol. However, when 5 mg/mL paclitaxel was included in the formulation, drug crystallization was noted very rapidly after preparation of the pre-emulsion, and the processed emulsions of Tween 80 and Myrj 52 were characterized as coarse, containing rod-shaped particles up to several microns in length, consistent with crystals of paclitaxel. Unlike the TPGS emulsion, which passed readily through a 0.22 micron filter with less than 1% loss of drug, the Tween and Myrj emulsions were unfilterable because of the presence of this crystalline drug material.

There are several possible explanations for the unexpected improvement of the α-tocopherol paclitaxel emulsions with TPGS. The drug has good solubility in TPGS, up to about 100 mg/mL. Most likely it is the strength of the affinity of paclitaxel benzyl side chains with the planar structure of the α-tocopherol phenolic ring in the TPGS molecule that stabilizes the complex of drug and carrier. In addition the succinate linker between the α-tocopherol and PEG tail is a novel -feature of this molecule that distinguishes its structure from other PEGylated surfactants tested.

Example 14
Poloxamer-based α-tocopherol Emulsion

| | |
|---|---|
| α-tocopherol | 6.0 gm % |
| Poloxamer 407 | 2.5 gm % |
| Ascorbyl Palmitate | 0.3 gm % |
| Sorbitol | 6.0 gm % |
| Triethanolamine | to pH 7.4 |
| Water | qs to 100 mL |

An α-tocopherol emulsion was prepared using Poloxamer 407 (BASF) as the primary surfactant. The white milky pre-mixture was homogenized with continuous recycling for 10 minutes at 25 Kpsi in a C5 homogenizer (Avestin, Ottawa Canada) with a feed temperature of 45° C. and a chiller loop for the product out set at 15° C. A fine, sterile filterable emulsion of α-tocopherol microparticles resulted. However, when this formulation was made with paclitaxel, precipitation of the paclitaxel was noted following overnight storage in the refrigerator, again underlying the superior utility of TPGS as the principle surfactant.

Example 15
Lyophilized Emulsion Formulation

Maltrin M100 (Grain Processing Corporation, Muscatine Iowa) was added as a 2× stock in water to the emulsion of Example 14. Aliquots were then frozen in a shell freezer and lyophilized under vacuum. On reconstitution with water, a fine emulsion was recovered.

Lyophilized formulations have utility where the indefinite shelf life of a lyophilized preparation is preferred. Lyophilizable formulations containing other saccharides, such as mannitol, albumin or PolyPep from Sigma Chemicals, St. Louis, Mo. can also be prepared.

Example 16
In vitro Release of Paclitaxel from α-tocopherol Emulsions

Figure 4:
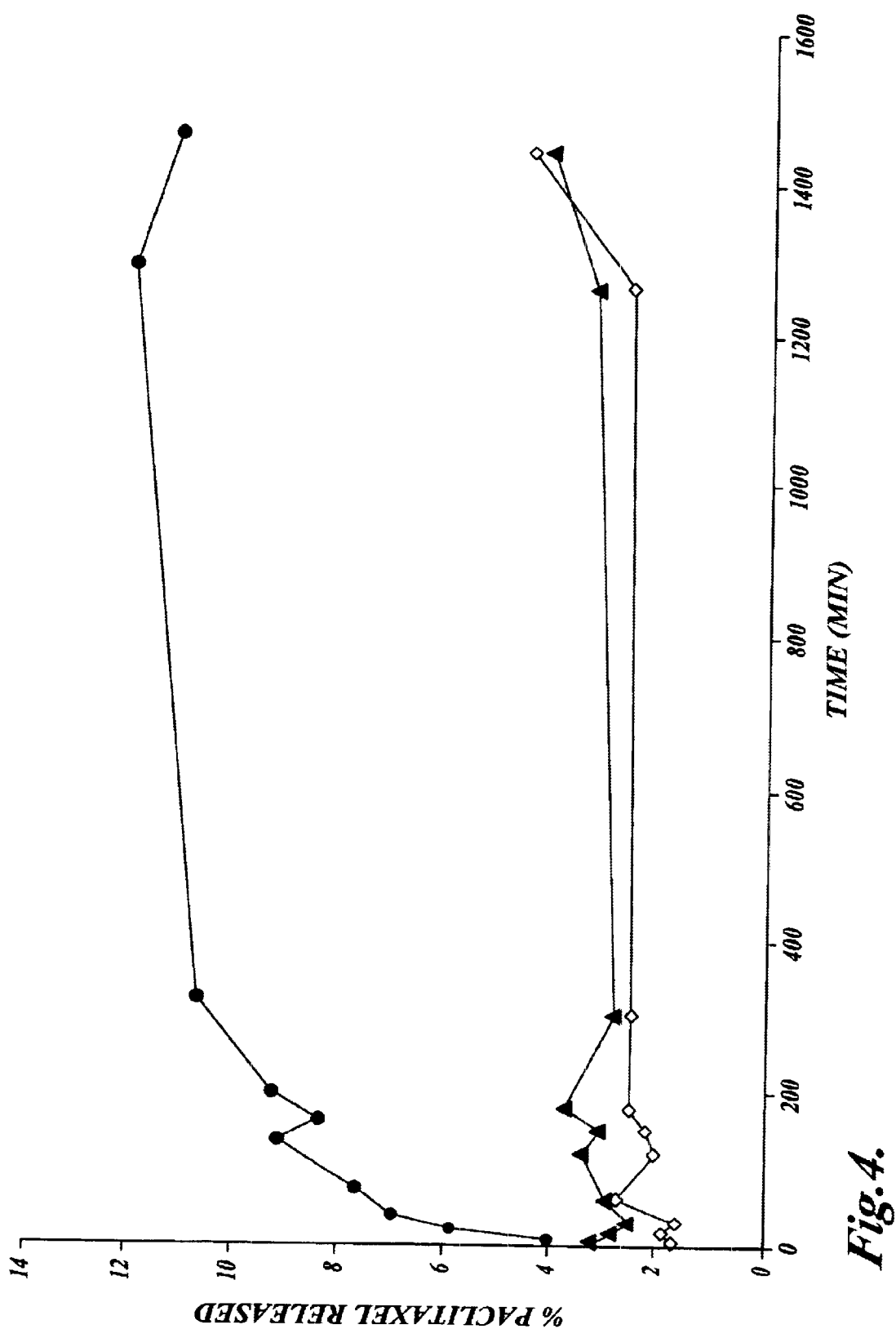
FIG. 4 shows the percentage of paclitaxel released over time from three different emulsions. The symbol • represents the percentage of paclitaxel released over time from an emulsion commercially available from Bristol Myers Squibb. The symbol ≡ represents the percentage of paclitaxel released over time from an emulsion of this invention containing 6 mg/ml paclitaxel (QWA) as described in Example 6. The symbol represents the percentage of paclitaxel released over time from an emulsion of this invention (QWB) containing 7 mg/ml paclitaxel as described in Example 7.

One of the desired characteristics of a drug delivery vehicle is to provide sustained release of the incorporated drug, a characteristic quite often correlated with improved pharmacokinetics and efficacy. In particular, long-circulating emulsions of paclitaxel can improve the delivery of the drug to cancer sites in the body. We have surprisingly found that the emulsions of the present invention do provide sustained release of paclitaxel when compared to the only FDA-approved formulation of paclitaxel at this time [Taxol®, Bristol Myers Squibb (BMS), Princeton N.J.]. Emulsions were prepared having paclitaxel concentrations of 6 mg/mL (QWA) and 7 mg/mL (QWB). For comparison, Taxol contains 6 mg/ml of paclitaxel dissolved in ethanol:cremophore EL 1:1 (v/v). In vitro release of paclitaxel from the different formulations into a solution of phosphate-buffered saline (PBS) at 37° C. was monitored using a dialysis membrane that is freely permeable to paclitaxel (MW cut-off of 10 kilodaltons). Quantification of the drug in pre- and post-dialysis samples was performed by HPLC. Drug release profiles in terms of both percent release and concentration of paclitaxel released over time were generated. As can be seen from the data in FIG. 4, less than 5% of paclitaxel was dialyzed from the emulsions over 24 hr, whereas about 12% was recovered outside the dialysis bag from the marketed BMS formulation. This indicates that drug release from the emulsion was significantly slowed relative to the commercially available solution.

Example 17
Biocompatibility of α-tocopherol Emulsions Containing Paclitaxel An acute single-dose toxicity study was performed. Mice 20–25 gm each were purchased and acclimatized in an approved animal facility. Groups of mice (n=3) received doses of the formulation containing from 30 to 90 mg/kg paclitaxel in the α-tocopherol emulsion prepared as described in Example 6. All injections were given intravenously by tailvein bolus.

Although all injections were given by bolus IV push, no deaths or immediate toxicity were observed at any dose, even at 90 mg/kg. The results for body weight are shown in Table 2. Weight loss was 17% in the highest group but all groups, even at 90 mg/kg, recovered or gained body weight over a period of 1.0 days post injection.

A vehicle toxicity study was also done. Animals receiving drug-free emulsion grew rapidly, and gained slightly more weight than animals receiving saline or not injected. This was attributed to the vitamin and calorie content of the formulation.

We observed a maximal tolerable dose (MTD) for paclitaxel of greater than 90 mg/kg (Table 2), with no adverse reactions noted. This is more than double the best literature values reported, in which deaths were observed at much smaller doses. The FDA-approved formulation of Taxol causes death in mice at bolus intravenous doses of 10 mg/kg, a finding repeated in our hands. In the rat, Taxol® was uniformly fatal at all dilutions and dose regimes we tested. In contrast, the composition of Example 6 was well tolerated in rats, and is even improved over Taxotere, a less toxic paclitaxel analogue commercially marketed by Rhone-Poulenc Rorer.

One possible explanation for the high drug tolerance is that the emulsion is behaving as a slow-release depot for the drug as suggested from the in vitro release data in Example 16.

TABLE 2

Average Body Weight Change of Mice Treated with Paclitaxel Emulsion

| Treatment (dose, mg/kg) | Number of Animals | BW Change (gm) Day 2 | BW Change (gm) Day 7 |
|---|---|---|---|
| Saline | 4 | 1.0 | 3.4 |
| Vehicle | 4 | 1.2 | 3.5 |
| Paclitaxel Emulsion (QWA) (36.3) | 2 | −1.0 | 2.2 |
| Paclitaxel Emulsion (QWA) (54.4) | 4 | −1.8 | 1.7 |
| Paclitaxel Emulsion (QWA) (72.6) | 4 | −1.5 | 1.6 |
| Paclitaxel Emulsion (QWA) (90.7) | 1 |  | −1.6 |

Example 18
Efficacy Evaluation of Paclitaxel Emulsion

The paclitaxel emulsion of Example 6 was also evaluated for efficacy against staged B16 melanoma tumors in nude mice and the data is shown in Table 3. Once again, the marketed product Taxol® was used as a reference formulation. Tumor cells were administered subcutaneously and therapy started by a tail vein injection at day 4 post-tumor administration at the indicated dosing schedule. Efficacy was expressed as percent increase in life-span (% ILS).

The following conclusions can be drawn from the data in Table 3: a) an increased life span of about 10% was obtained by administration of BMS Taxol at 10 mg/kg Q2D×4, b) %ILS values improved to 30–50% by administration of the α-tocopherol emulsion of paclitaxel at 30, 40 or 50 mg/kg Q2D×4, dose levels made possible by the higher MTD, c) a nice dose response was observed when the emulsion was administered at 30, 50 and 70 mg/kg Q4D×3,:with about 80% ILS being-observed at 70 mg/kg and, d) even at 90 mg/kg dosed only once at day 4, there was about 36% ILS. These data clearly illustrate the potential of the emulsions of the present invention to substantially improve the efficacy of paclitaxel.

Example 19
Efficacy Evaluation of Paclitaxel Emulsions

The emulsions of examples 6, 7 and 8 (QWA, QWB and QWC respectively) were compared for efficacy against B16 melanoma in mice; Taxol® was again used as a reference formulation. Methods essentially identical to those of Example 18 were used. The data from this study is summarized in Table 3. Efficacy was expressed as: a) percent tumor growth inhibition (% T/C, where T and C stand for treated and control animals, respectively); b) tumor growth delay value (T-C), and c) log cell kill which is defined as the ratio of the T-C value over 3.32 ×tumor doubling time. The latter parameter for this particular tumor model was calculated to be 1.75 days. As can be seen from the results in Table 4, all measures of efficacy: tumor growth inhibition, tumor growth delay value and log cell kill demonstrate superior efficacy of α-tocopherol emulsions as a drug delivery vehicle over Taxol®, particularly when the emulsions were dosed every four days, at 70 mg/kg. As explained in Example 16, this increased efficacy is likely a result of improved drug biocompatibility and/or sustained release.

TABLE 3

Survival of Mice with B16 Tumors Treated with QWA and Taxol ®

| Treatment Group & Schedule | Mean Survival Time, Days (Mean ± S.E.M[a]) | % ILS[b] (vs vehicle) (Mean ± S.E.M) |
|---|---|---|
| Vehicle Control (Days 4, 8, 12) | 13.2 ± 0.9 | — |
| Saline Control (Days 4, 8, 12) | 15.8 ± 1.2 | 19.7 ± 8.6 |
| Taxol (10 mg/kg) (Days 4, 6, 8, 10) | 16.4 ± 10.7 | 24.2 ± 5.4 |
| QWA (30 mg/kg) (Days 4, 6, 8) | 19.2 ± 1.4 | 45.4 ± 10.3 |
| QWA (40 mg/kg) (Days 4, 6, 8) | 21.3 ± 1.4 | 61.4 ± 10.3 |
| QWA (50 mg/kg) (Days 4, 6, 8) | 18.8 ± 0.7 | 42.4 ± 5.7 |
| QWA (30 mg/kg) (Days 4, 8, 12) | 15.3 ± 0.8 | 15.9 ± 6.4 |
| QWA (50 mg/kg) (Days 4, 8, 12) | 20.7 ± 1.3 | 56.8 ± 9.5 |
| QWA (70 mg/kg) (Days 4, 8, 12) | 24.2 ± 0.9 | 83.3 ± 6.4 |
| QWA (90 mg/kg) (Day 4 only) | 18.0 ± 0.6 | 36.4 ± 4.4 |

[a]SEM = Standard Error of Mean
[b]% ILS = % Increase in Lifespan = [(T − C)/C] × 100 where:
T = mean survival of treated
C = mean survival of control according to the NCI standards an ILS value greater than 50% indicates significant anti-tumor activity.

Example 20
Self-emulsification of an α-tocopherol/Tagat TO Mixture

α-tocopherol 2.0. gm and Tagat TO (Goldschmidt Chemical Corp, Hopewell Va.) 800 mg were dissolved together. About 80 mg of the oily mixture was transferred to a test tube and water was then added. With gentle hand mixing, there was immediate development of a rich milky emulsion, consistent with "self-emulsifying systems" proposed as drug delivery systems, in which surfactant-oil mixtures spontaneously form an emulsion upon exposure to aqueous media.

Example 21
Self-emulsifying Formulation Containing Paclitaxel

Paclitaxel 50 mg/ml was prepared in α-tocopherol by the method described in Example 1. Tagat TO 20% (w/w) was added. The resultant mixture was clear, viscous and amber in color. A 100 mg quantity of the oily mixture was transferred to a test tube. On addition of 1 mL of water, with vortex mixing, a fine emulsion resulted.

Example 22
Self-emulsifying Formulation of Paclitaxel

Paclitaxel 50 mg/ml was prepared in α-tocopherol by the method described in Example 1. After removal of the ethanol under vacuum, 20% TPGS and 10% polyoxyethyleneglycol 200 (Sigma Chemical Co) were added by weight. A demonstration of the self-emulsification ability of this system was then performed by adding 20 mL of deionized water to 100 mg of the oily mixture at 37° C. Upon gentle mixing, a white, thin emulsion formed, consisting of fine emulsion particles demonstrated with the Malvern Mastersizer (Malvern Instruments Worcester Mass.) to have a mean size of 2 microns, and a cumulative distribution 90% of which was less than 10 microns.

Example 23
Etoposide Emulsion Formulation in α-tocopherol

Etoposide 4 mg (Sigma Chemical Co) was dissolved in the following surfactant-oil mixture:

TABLE 4

Comparison of 3 paclitaxel emulsions and Taxol against early-stage B16 melanoma

| Test Article | Dosage mg/kg/day | Dosing Schedule (days) | Total Dose (mg/kg) | Median tumor wt. on day 15 (mg) | Median tumor wt. on day 18 mg (range) | % T/C Day 15 | T-C (days) | Log cell kill total |
|---|---|---|---|---|---|---|---|---|
| Control | 0 | 4,6,8,10 | 0 | 836 | 2139 | — | — | — |
| Taxol ® | 20 | 4,6,8,10 | 80 | 383 | 1217 | 46 | 2 | 0.34 |
| QWA | 20 | 4,6,8,10 | 80 | 381 | 1197 | 46 | 2 | 0.34 |
| QWA | 40 | 4,6,8,10 | 160 | 104 | 306 | 12 | 7 | 1.2 |
| QWA | 70 | 4,8,12,16,20 | 350 | 15 | 11 | ~2 | | |
| QWB | 20 | 4,6,8,10 | 80 | 197 | 653 | 24 | 5 | 0.86 |
| QWB | 30 | 4,6,8,10 | 120 | 139 | 449 | 17 | 5 | 0.86 |
| QWB | 40 | Toxic | | | | | | |
| QWC | 20 | 4,6,8,10 | 80 | 319 | 848 | 34 | 3 | 0.52 |
| QWC | 40 | 4,6,8,10 | 160 | 53 | 194 | 6 | 8 | 1.4 |
| QWC | 70 | 4,8,12,16,20 | 350 | 33 | 66 | 4 | >15 | >2.6 |

Tumor Doubling Time calculated to be 1.75 days.
% T/C = Tumor Growth Inhibition (Day 15) = (median tumor wt. of treated/median tumor wt. control) × 100
T-C = Tumor Growth Delay value = median time for treatment group (T) and control group (C) tumors to reach a predetermined size (usually 750–1000 mg)
Log cell kill = (T-C value)/(3.32 × tumor doubling time)

| | |
|---|---|
| Etoposide | 4 mg |
| α-tocopherol | 300 mg |
| TPGS | 50 mg |
| Poloxamer 407 | 50 mg |

Ethanol and gentle warming was used to form a clear amber solution of drug in oil. The ethanol was then removed under vacuum.

A pre-emulsion was formed by adding 4.5 mL of water containing 4% sorbitol and 100 mg TPGS at 45° C. with sonication. The particle size was further reduced by processing in an Emulsiflex 1000 (Avestin,Ottawa Canada). The body of the Emulsiflex 1000 was fitted with a pair of 5 mL syringes and the entire apparatus heated to 45° C. before use. The 5 mL of emulsion was then passed through it by hand approximately 10 times. A free flowing, practical emulsion of etoposide in an α-tocopherol vehicle resulted.

We note that the solubilized form of etoposide in α-tocopherol can also be used as an oral dosage form by adaption of the methods of the preceding examples.

Example 24
Dissolution of Ibuprofen or Griseofulvin in α-tocopherol

Ibuprofen is a pain-killer, and may be administered by injection when required if there is danger that the drug will irritate the stomach. The following solution of ibuprofen in α-tocopherol may be emulsified for intravenous administration.

Ibuprofen (Sigma Chemicals), 12 mg. crystalline, dissolved without solvent in α-tocopherol, 120 mg, by gentle heating. The resultant 10% solution of ibuprofen in vitamin E can be emulsified by the method s described in Examples 4, 6, 7, 8 or 22.

An antifungal compound, griseofulvin, 12 mg, was first dissolved in 3 mL of anhydrous ethanol; α-tocopherol was then added, 180 mg, and the ethanol was removed with gentle heating under vacuum. The resultant solution of griseofulvin in α-tocopherol is clear and can be emulsified by the methods described in Examples 4, 6, 7, 8 or 22.

Example 25
Vitamin E Succinate Emulsion Formulation

Vitamin E succinate has been suggested as a therapeutic for the treatment of lymphomas and leukemias and for the chemoprevention of cancer. The following is a composition and method for the emulsification of vitamin E succinate in α-tocopherol. Sucrose ester S1170 is a product of Mitsubishi Kagaku Foods,Corp, Tokyo Japan. Vitamin E succinate, as the free acid, was obtained as a whitish powder from ICN Biomedicals, Aurora, Ohio. Emulsions incorporating other surfactants such as pluronics, and TPGS along with α-tocopherol and α-tocopherol succinate can be prepared in a similar manner with and without a therapeutic agent.

α-Tocopherol 8 gm and vitamin E succinate 0.8 gm were dissolved together in ethanol in a round bottom flask. After removal of the solvent, 100 mL of an aqueous buffer was added. The alkaline buffer consisting of 2% glycerol, 10 mM triethanolamine, and 0.5 gm % sucrose ester S1170. After mixing for 2 min, the pre-emulsion was transferred to an Avestin Model C-5homogenizer and homogenization was continued for about 12 minutes at a process feed temperature of 58° C. The pressure differential across the interaction head was 25 to 26 kpsi. During homogenization, pH was carefully monitored, and adjusted as required to pH 7.0. Care was taken to exclude oxygen during the process. A fine white emulsion resulted.

Example 26
α-tocopherol Levels in Esters

Levels of α-tocopherol in commercially available esters: tocopherol-acetate, -succinate, -nicotinate, -phosphate and TPGS were either provided by the vendor or determined by HPLC. The concentration of free α-tocopherol in these solutions is less than 1.0%, generally less than 0.5%.

Example 27
Resveratrol Emulsion Formulation

Resveratrol is a cancer chemopreventative first discovered as an extract of grape skins. It has been proposed as a dietary supplement.

Resveratrol was obtained from Sigma Chemical Co. While it dissolved poorly in ethanol, upon addition of 10 mg resveratrol, 100 mg of α-tocopherol, 100 mg TPGS and ethanol, a clear solution formed rapidly. Upon removal of the ethanol, a clear amber oil remained.

The oily solution of resveratrol can be formulated as a self-emulsifying system for oral delivery by the various methods of the preceding examples.

Example 28
Muramyl Dipeptide Formulation

Muramyl dipeptides are derived from mycobacteria and are potent immunostimulants representative of the class of muramyl peptides, mycolic acid and lipopolysaccharides. They have use, for example, in the treatment of cancer, by stimulating the immune system to target and remove the cancer, particularly in connection with anti-cancer vaccines. More recently, muroctasin, asynthetic analog, has been proposed to reduce non-specificside effects of the bacterial wall extracts.

N-acetylmuramyl-6-O-steroyl-1-alanyl-d-isoglutamine was purchased from Sigma Chemical Co. and 10 mg was dissolved in 100 mg α-tocopherol and 80 mg TPGS. Ethanol was used as a co-solvent to aid in dissolution of the dipeptide, but was removed by evaporation under vacuum, leaving a clear solution in α-tocopherol and surfactant.

This oil solution of the drug can be emulsified for parenteral administration by the various methods of the preceding examples.

Example 29
Alcohol-containing Emulsion

In attempting to adapt the teachings of PCT WO 95/11039 to the oral administration of paclitaxel, the following formulation was made.

| | |
|---|---|
| paclitaxel | 0.125 gm |
| α-Tocopherol | 0.325 gm |
| TPGS | 0.425 gm |
| Ethanol | 0.125 gm |

As before, paclitaxel was dissolved in a α-tocopherol and TPGS with ethanol, which was then removed under vacuum. By dry weight, residual ethanol was less than 3 mg (0.3% w/w). Fresh anhydrous ethanol 0.125 gm was then added back to the formulation. After mixing, the suitability of the formulation for oral administration, as in a gelatin capsule, was simulated by the following experiment. An aliquot of 100 mg of the free-flowing oil was added to 20 mL of water at 37° C. and mixed gently with a vortex mixer. A fine emulsion resulted. But after twenty minutes, microscopy revealed the growth of large numbers of crystals in rosettes, characteristic of paclitaxel precipitation. It was concluded that this formulation was not suitable for oral administration of paclitaxel because large amounts of the drug would be in the form of crystals on entry into the duodenum, where it would be prevented from uptake because of its physical form. We speculate that the excess of ethanol, in combination with the high ratio of TPGS to α-tocopherol, is responsible for the observed crystallization of the drug from this formulation.

Example 30

Alcohol-containing α-tocopherol Emulsion

In attempting to adapt the teachings of PCT WO 95/11039 to the intravenous administration of paclitaxel, the following formulation was made:

| | |
|---|---|
| paclitaxel | 0.050 gm |
| α-tocopherol | 0.100 gm |
| Lecithin | 0.200 gm |
| Ethanol | 0.100 gm |
| Butanol | 0.500 gm |

As before, paclitaxel was dissolved in α-tocopherol and TPGS with ethanol, which was then removed under vacuum. By dry weight, residual ethanol was less than 2 mg (0.5% w/w). Fresh anhydrous ethanol 0.100 gm and n-butanol 0.500 gm was then added back to the formulation. A clear oil resulted. The injection concentrate was tested for biocompatibility in administration by standard pharmaceutical practice of admixture with saline. About 200 mg of the oil was placed into 20 mL of saline and mixed. Large flakes of insoluble material developed immediately and the greatest amount of material formed dense deposits on the walls of the test tube. The mixture was clearly unsuitable for parenteral administration by any route, and we speculate that this is so regardless of the identity of the drug contained in the formulation. By trial and error we have learned that lecithin is a poor choice as surfactant for α-tocopherol by virtue of its low HLB (around 4). Other successful examples described here for fine emulsions suitable for parenteral administration were all made with high HLB surfactants. These surfactants include TPGS (HLB around 17), Poloxamer 407 (HLB about 22) and Tagat TO (HLB about 14.0). In general, we found that α-tocopherol emulsification is best performed with principal surfactants of HLB>10, preferably greater than 12. Lecithin is not in this class, although it could be used as a co-surfactant. In comparison, typical o/w emulsions of triglycerides are made with surfactants of HLB between 7 and 12, demonstrating that α-tocopherol emulsions are a unique class by virtue of the polarity and extreme hydrophobicity of the α-tocopherol, factors that also favor the solubility of lipophilic and slightly polar lipophilic drugs in α-tocopherol. See *Emulsions: Theory and Practice*, 2nd Ed. p.248 (1985).

Example 31

Various formulations useful in the invention (Table 5) are prepared as follows:

TABLE 5

| Composition of Injectable | A (split surfactant) | | B (all surfactant in oil) | |
|---|---|---|---|---|
| Paclitaxel Emulsions | Weight (g) | Weight (%) | Weight (g) | Weight (%) |
| Oil Phase | | | | |
| Paclitaxel | 0.50 | 0.51 | 0.53 | 0.52 |
| PEG 400 | 6.02 | 6.04 | 6.38 | 6.30 |
| TPGS | 3.78 | 3.80 | 5.32 | 5.25 |
| Pluronic F127 | | | 1.07 | 1.05 |
| Vitamin E | 8.04 | 8.07 | 8.51 | 8.40 |
| Aqueous Phase | | | | |
| TPGS | 1.25 | 1.26 | | |
| Pluronic F127 | 1.01 | 1.01 | | |
| Water | 79.00 | 79.31 | 79.50 | 78.48 |
| Total | 99.60 | 100.00 | 101.30 | 100.00 |

Formulation A—Split Surfactants:
1) 1.25 g TPGS and 1.01 g Pluronic F127 were dissolved in 79.00 g water for injection by heating and stirring.
2) 0.533 g paclitaxel was dissolved in 6.354 g PEG 400 by mixing (low shear) at 75° C.
3) 3.992 g TPGS and 8.490 g Vitamin E were added and mixed (low shear) at 45° C. until TPGS was melted and the mixture was visibly homogeneous. This oil phase represents a slight excess in order to account for incomplete transfer in Step 4.
4) The aqueous phase (step 1) was heated to 45° C. and mixed at medium shear (laboratory mixing motor) while 45° C. oil phase (step 2+3) was poured in over 1 minute. Mixing was continued 2 minutes more to form a crude emulsion.
5) The emulsion was homogenized in an Avestin C5 in continuous recycle mode for 1 hour at 22 Kpsi peak stroke pressure.
6) Actual amounts and percentages shown in the table are corrected for the incomplete transfer of oil phase during Step 4.

This method utilizing the split surfactants is useful in the cases where the solubility of a particular surfactant in the oil phase is limited.

Formulation B—All Surfactants in Oil Phase
1) 1.066 g paclitaxel was dissolved in 12.887 g PEG400 by mixing (low shear at 75° C.
2) 10.739 g TPGS and 2.157 g Pluronic F127 were added and mixed (low shear) at 50–60° C. until both surfactants were completely melted/dissolved.
3) 17.176 g Vitamin E was added and mixed (low shear) at 45–50° C. until the mixture was visibly homogeneous.
4) 21.8 g of the oil phase produced in Steps 1–4 was added over 1 minute to 79.5 g water while mixing at medium shear (laboratory mixing motor). Mixing was continued for a total of 3 minutes to form a crude emulsion.
5) Emulsion was homogenized in an Avestin C5 in continuous recycle mode for 30 minutes at 22 K psi peak stroke pressures From a processing perspective it is advantageous to have all of the surfactants in the oil phase. Both the dispersion of the pre-emulsion and subsequent homogenization are facilitated and potential gellation of high melting point surfactants, such as TPGS, can be avoided.

Example 32
Etoposide Emulsion

A vitamin E emulsion (6.0% vitamin E, 3.5% TPGS, 6.0%, PEG400, 8% Pluronic F-127) and incorporating 2 mg/ml of Etoposide was prepared as follows:
1) 0.1044 g of Etoposide was dissolved in 3.1435 g of PEG 400 (5 min at 65° C.).
2) 2.0447 g of TPGS and 3.1563 g of Vitamin E were added and mixed until complete dissolution.
3) The oil phase was mixed at 44° C. with 42.4 g of water for injection incorporating 0.5 g of Pluronic F-127 (the aqueous phase was degassed by boiling prior to its mixing with the oil phase) and the pre-emulsion was formed by brief sonication.
4) Upon homogenization in an Avestin CS at 22–24 Kpsi a fine emulsion was formed.

Example 33
Etoposide Emulsion

An α-Tocopherol emulsion containing PEG 300 and incorporating 2 mg/ml of Etoposide was prepared as follows:

Etoposide was first dissolved in PEG-300 (10 min at 72° C.). TPGS and Vitamin E were then added to the drug solution. Aqueous phase (WFI containing Poloxamer 407) was degassed by boiling prior to use. Pre-emulsion was prepared by adding 5 g of the oil phase to 45 g of water at 45° C. After a 3-min mixing the pre-emulsion was homogenized at 25 Kpsi for 30 min to produce a fine emulsion. The final composition of the emulsion is shown below:

| Component | Composition (%, w/w) |
|---|---|
| Etoposide | 0.2 |
| Vitamin E | 3.0 |
| TPGS | 1.5 |
| PEG-300 | 3.0 |
| Poloxamer 407 | 1.0 |
| WFI (water for injection) | 92.3 |

Example 34

Additional paclitaxel emulsions for injection are presented in Table 6.

TABLE 6

Composition of Injectable paclitaxel emulsions

| Composition of Injectable | C (split surfactant) | | D (all surfactant in oil) | | E (all surfactant in oil) | |
|---|---|---|---|---|---|---|
| Paclitaxel Emulsions | Weight (g) | Weight (%) | Weight (g) | Weight (%) | Weight (g) | Weight (%) |
| Oil Phase | | | | | | |
| Paclitaxel | 2.0 | 0.4 | 0.55 | 1.1 | 0.5 | 0.5 |
| PEG 400 | 32.0 | 6.4 | 3.36 | 6.7 | 10.0 | 10.0 |
| TPGS | 18.85 | 3.77 | 2.60 | 5.2 | 4.3 | 4.3 |
| Pluronic F127 | | | 0.52 | 1.0 | 5.1 | 1.1 |
| Vitamin E | 40.5 | 8.1 | 4.19 | 8.4 | 7.2 | 7.2 |

TABLE 6-continued

Composition of Injectable paclitaxel emulsions

| Composition of Injectable | C (split surfactant) | | D (all surfactant in oil) | | E (all surfactant in oil) | |
|---|---|---|---|---|---|---|
| Paclitaxel Emulsions | Weight (g) | Weight (%) | Weight (g) | Weight (%) | Weight (g) | Weight (%) |
| Aqueous Phase | | | | | | |
| TPGS | 6.4 | 1.28 | | | | |
| Pluronic F127 | 5.0 | 1.0 | | | | |
| Water | 395.25 | 79.05 | 41.0 | 82.0 | 79.5 | 79.5 |
| Total | 500.0 | 100.0 | 52.2 | 104.4 | 102.6 | 102.6 |

Example 35

Compositions of various self-emulsifying emulsions useful in this invention are shown in Table 7.

TABLE 7

Self-Emulsifying Emulsions

| Composition of Self-Emulsifying Emulsions | SEFP-1 | | SEFP-2 | |
|---|---|---|---|---|
| | Weight (g) | Weight (%) | Weight (g) | Weight (%) |
| Paclitaxel | 0.255 | 5.11 | 0.258 | 5.14 |
| Vitamin E | 1.989 | 19.88 | 2.242 | 44.70 |
| TPGS | 0.992 | 19.99 | 0.765 | 15.25 |
| PEG 400 | 1.502 | 30.11 | 0.999 | 19.92 |
| Pluronic F127 | 0.250 | 5.01 | | |
| Solutol HS15 | | | 0.752 | 14.99 |
| Total | 4.988 | 100.00 | 5.016 | 100.00 |

The emulsions described in Table 7 were synthesized as follows.

SEFP-1

Paclitaxel and PEG 400 were heated together at 60–67° C. and stirred until the drug was dissolved in PEG (15 min). Then TPGS and Pluronic F127 were added and stirred at 70·C for 10–15 min to dissolve the surfactant. Finally, Vitamin E (α-tocopherol) was added and mixed for 5–10 min at 55° C. until the mixture was clear and homogeneous. Upon dilution with an aqueous phase a fine emulsion can be obtained.

SEFP-2

Paclitaxel and PEG 400 were first stirred at 65–75° C. for 45 min there TPGS was added and stirring was continued for another 30 min to completely dissolved all three components and produced a clear solution. Finally Solutol HS-15 and Vitamin E were added and mixed for about min at 55° C. to obtain a clear homogeneous liquid. Upon dilution with an aqueous phase a fine emulsion can be obtained.

Example 36

Additional compositions of self-emulsifying emulsions of paclitaxel are shown in Table 8.

TABLE 8

| Composition of Self-Emulsifying Emulsions | Self-Emulsifying Emulsions | | | |
|---|---|---|---|---|
| | SEFP-1 | | SEFP-2 | |
| | Weight (g) | Weight (%) | Weight (g) | Weight (%) |
| Paclitaxel | 0.10 | 2 | 0.05 | 1 |
| α-Tocopherol | 1.40 | 28 | 0.50 | 10 |
| TPGS | 1.00 | 20 | 0.95 | 19 |
| PEG400 | 1.00 | 20 | 1.00 | 20 |
| Solutol HS-15 | 1.50 | 30 | 2.50 | 50 |
| Total | 5.00 | 100 | 5.00 | 100 |

SEFP-3 and SEFP-4 were prepared by first dissolving paclitaxel in solutol HS-15+PEG 400 by low shear mixing at 60–70° C. (<30 min), TPGS and α-tocopherol were then added and briefly mixed to form a clear solution TPGS solidification can be observed at room temperature but remains a clear liquid at 37° C.

The particle size of the emulsions upon dilution of SEFP-3 and SEFP4 was determined as follows: 0.2 ml of SEFP-3 or SEFP-4 was diluted in 100 ml of Phosphate-buffered Saline at 37° C. by low shear mixing with a stir bar for minutes. An emulsion was quickly formed, the particle size of which was measured by the Malvern Mastersizer. The volume mean diameter of SEFP-3 and SEFP-4 was found to be, 2.49 and 1.55 $\mu$m, respectively.

For an efficient self-emulsified system the mean droplet diameter of the resulting emulsion should be less than 10 $\mu$m and preferably less than 5 $\mu$m.

Example 37

Paclitaxel Emulsions Incorporating a Pegylated Phospholipid

DMPE-PEG$_{2000}$(Dimyristoyl Phosphatidyl Ethanolamine—Polyethylene Glycol 2000). incorporating emulsions were prepared (Table 9). Paclitaxel, when present, was first dissolved in PEG 400 by low shear mixing at 75° C. The other ingredients were added and briefly mixed (after melting TPGS, and in the case of DMPEG-2, the P407) to form a clear solution. A vacuum was applied to de gas the oil phase prior to emulsification, and the oil phase was brought to 45° C. Water was boiled for 15 minutes to degas, then brought to 45° C. also. The two phases were mixed at 45° C. at low to medium shear to form a pie-emulsion. For formulations DMPE-PEG-P2, DMPE-PEG-P3 and DMPE-PEGP-4, this was accomplished by simply adding the warm water to the oil phase and swirling by hand with sonication. The pre-emulsion for DMPE-PEG2 was prepared by pouring oil phase into water while stirring with a laboratory mixing motor. Pre-emulsions were immediately hormogenized in the Avestin Chomogenizer at 20–22K psi peak stroke pressure to produce fine emulsions with a mean droplet diameters and 99% cumulative distributions of less than 200 nm.

TABLE 9

| Paclitaxel Emulsions Incorporating a Pegylated Phospholipid | | | | | | | | |
|---|---|---|---|---|---|---|---|---|
| | DMPE-PEG-1 | | DMPE-PEG-2 | | DMPE-PEG-3 | | DMPE-PEG-4 | |
| | (g) | (%) | (g) | (%) | (g) | (%) | (g) | (%) |
| Paclitaxel | 0.53 | 1.1 | 0.96 | 1.0 | | | | |
| PEG 400 | 3.07 | 6.1 | 5.77 | 5.8 | 1.8 | 6.0 | 1.84 | 6.1 |
| TPGS | 2.59 | 5.1 | 4.62 | 4.7 | 1.51 | 5.0 | 1.22 | 4.1 |
| DMPE-PEG$_{2000}$ | 0.53 | 1.1 | 0.20 | 0.2 | 0.30 | 1.0 | 0.62 | 2.1 |
| Poloxamer 407 | | | 0.96 | 1.0 | | | | |
| Vitamin E | 4.11 | 8.2 | 7.71 | 7.8 | 2.42 | 8.1 | 2.14 | 7.2 |
| Water | 39.50 | 78.5 | 79.00 | 79.6 | 24.0 | 79.9 | 24.1 | 80.5 |
| Total | 50.33 | 100.0 | 99.23 | 100.0 | 30.03 | 100.0 | 29.92 | 100 |

Example 37

Efficacy Data

Figure 5:
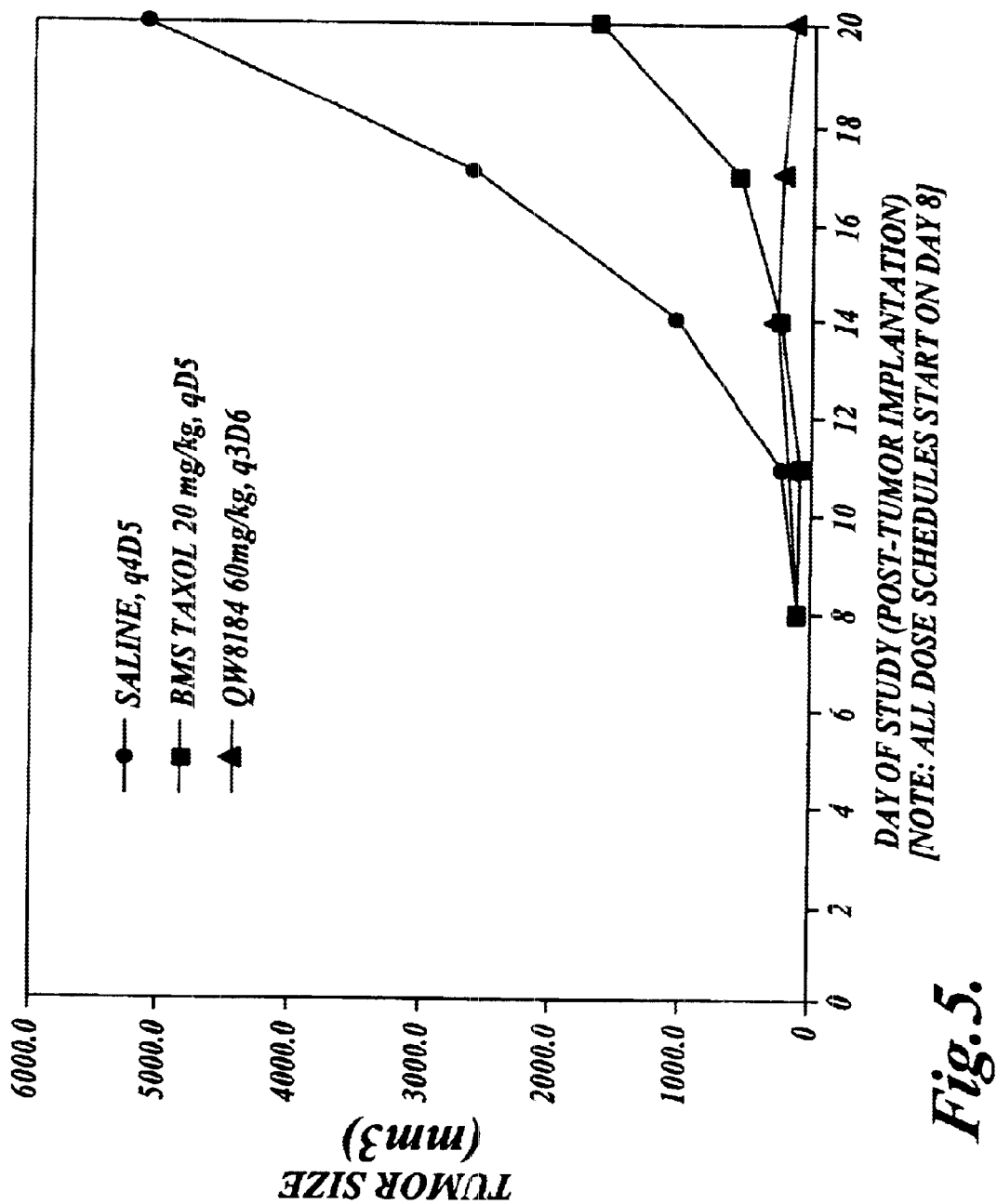
FIG. 5 shows the efficacy of a PEG-400/Vitamin E/paclitaxel emulsion against B16 melanoma in mice.

Formulation D (Table 6) was evaluated for efficacy against B16 melanoma in mice as described in Examples 18 and 19 and the data is summarized in FIG. 5. Comparative efficacy data is presented in Table 10.

TABLE 10

Comparative Efficacy in B16 Melanoma Tumor Model:
Taxol ® vs SONUS Paclitaxel Emulsion "QW 8184"

| Test Article | Dosage (mg/kg/day) | Schedule (days) | Total Dose (mg/kg) | Median Tumor Weight on Day | | | | | | % Mortality (by day 17) | % T/C Day 13 | T-C (days) | Log cell kill |
|---|---|---|---|---|---|---|---|---|---|---|---|---|---|
| | | | | 1 | 4 | 7 | 10 | 13 | 17 | | | | |
| Saline | 80 equiv. | q4dx5 | — | 80 | 245 | 1271 | 1800 | 2916 | 14114 | 60 | — | — | — |
| Taxol ® | 20 | qdx5 | 100 | 69 | 123 | 331 | 2 | 2192 | 4901 | 20 | 75 | 5 | 0.9 |
| Formulation D | 60 | q3dx5 | 300 | 108 | 106 | 221 | 234 | 400 | 400 | 60 | 14 | 13 | 2.3 |

% T/C = Tumor Growth Inhibition (median tumor wt. of treated/median tumor wt. control) × 100
T-C = Tumor Growth Delay value (median time for treatment group (T) and control group tumors (C) to reach a predetermined size (>750 mg)
Log cell kill = (T-C value)/(3.32 × tumor doubling time) tumor doubling time calculated to be 1.75 days.

Consistent with the data in Table 4, efficacy assessment by tumor growth inhibition, tumor growth delay and log cell kill indicate significant improvement with Formulation D over Taxol®.

Example 38

Physical Stability Data

The physical stability of formulation D was assessed by potential particle size changes upon storage and the data is shown in Table 11.

TABLE 11

Physical Stability of Formulation D

| Storage Day (2–8° C.) | Volume-weighted Particle Size (nm) | |
|---|---|---|
| | Mean Droplet Diameter | Distribution 99% of the Particles less than |
| 2 | 71.3 | 154.6 |
| 3 | 69.3 | 151.8 |
| 10 | 67.7 | 151.6 |
| 15 | 69.8 | 150.8 |
| 28 | 66.3 | 152.3 |
| 30 | 66.9 | 150.3 |

Particle size was measured using the Nicomp 370 submicron particle size analyzer. As can be seen from the data in Table 11 no significant changes were observed in either the mean droplet diameter or the 99% cumulative distribution of the particles. The later parameter is often used as an indicator of particle aggregation and growth. In addition, no precipitation or other gross changes were observed during storage. Long term stability is ongoing.

Example 39
Chemical Stability

The chemical stability of formation D (Table 6) was monitored by HPLC using the procedures of Example 5 and the data is shown in Table 12. HPLC is utilized to quantitate the concentration of paclitaxel and degradants. In Table 12, drug concentration is equivalent to drug potency.

TABLE 12

Chemical Stability of Formulation D

| Storage Day (2–8° C.) | Drug Concentration (mg/ml) |
|---|---|
| 0 | 9.53 |
| 10 | 9.54 |
| 19 | 9.39 |
| 32 | 9.54 |

It is evident from this data that the drug potency in formulation D remains unchanged under these storage conditions.

In addition, no degradation of the drug was observed during this storage time.

Example 40
Emulsions Containing PEG 300 or NMP

α-Tocopherol emulsions containing PEG 300 or NMP (N-Methyl-2-pyrrolidone) and incorporating 10 mg/ml paclitaxel are shown in Table 13.

TABLE 13

| | PEG 300 | | NMP | |
|---|---|---|---|---|
| Component | Weight (g) | Weight % | Weight (g) | Weight % |
| Paclitaxel | 0.05 | 1.0 | 0.05 | 1.0 |
| PEG 300 | 0.32 | 6.2 | | |
| NMP (N-Methyl-2-pyrrolidone) | | | 0.18 | 3.6 |
| TPGS | 0.25 | 4.9 | 0.25 | 5.0 |
| Poloxamer 407 | 0.05 | 0.9 | 0.05 | 1.0 |

TABLE 13-continued

| | PEG 300 | | NMP | |
|---|---|---|---|---|
| Component | Weight (g) | Weight % | Weight (g) | Weight % |
| Vitamin E | 0.40 | 7.9 | 0.43 | 8.7 |
| Water | 4.00 | 78.9 | 4.00 | 80.7 |
| Total | 5.07 | 100.0 | 4.96 | 100.0 |

In both cases, paclitaxel was first dissolved in the solvent (PEG 300 or NMP) with low shear mixing. Heating to 60° C. was used with the PEG 300 to speed the dissolution while with the NMP formulation a few minutes at room temperature was sufficient to dissolve the drug. The remaining ingredients (except water) were then added and the mixtures were heated to 60–65° C. with low shear mixing to melt the solid surfactant and produce homogeneous, clear solutions. The solutions were brought to 45° C., then 45° C. water was added to them. The resulting mixtures were processed under medium shear to produce a thick, white crude emulsion, very similar in appearance to the pre-emulsion of formulation D (Table 6). These emulsions can further be homogenized at high pressure to produce fine emulsions.

Example 41

Large Scale Preparation of Formulation D (QW8184)

Using procedures analogous to those described in previous examples, formulation D (Table 6) was manufactured at a large scale in 2×2 L sub-lots having the following composition (the shaded area represents the oil and aqueous phase content of the emulsion):

TABLE 14

| | Sub-Lot 1 | | Sub-Lot 2 | |
|---|---|---|---|---|
| Component | Amount in Oil Phase (g) | Weight (%) | Amount in Oil Phase (g) | Weight (%) |
| Paclitaxel | 21 | 1.01 | 21 | 1.01 |
| PEG400 | 123.6 | 5.96 | 123.6 | 5.92 |
| α-Tocopherol | 164.8 | 7.94 | 164.8 | 7.89 |
| TPGS | 103 | 4.97 | 103 | 4.93 |
| Poloxamer 407 | 20.6 | 0.99 | 20.6 | 0.99 |
| Oil Phase Total | 433 | 20.97 | 413.2 | 20.73 |

For the preparation of the pre-emulsion, 416.8 g of the oil phase of sub-lot 1 and 413.2 g of the oil phase of sub-lot 2 were mixed with 1580 g of water for injection (5 min at 46° C.). Upon homogenization fine emulsions were produced having a mean droplet diameter of about 70 nm, that is, very similar to that of formulation D at the small scale (Table 11). This scaled formulation was further sterilized by filtration through a 0.2 micron filter.

Example 42

Hemolytic Activity Evaluation of a Drug-Free Emulsion

A large scale (2.5 L) of formulation D in the absence of paclitaxel was prepared as described in Example 41 having the following composition.

TABLE 15

| Component | Amount in Oil Phase (g) | Weight % |
|---|---|---|
| PEG400 | 154.5 | 5/97 |
| α-Tocopherol | 206 | 7.96 |
| TPGS | 128.8 | 4.97 |
| Poloxamer 407 | 25.8 | 1.00 |
| Oil Phase Total | 515.1 | 19.89 |

For the preparation of the pre-emulsion, 496.7 g of the oil phase were mixed with 2000 g of water for injection (5 min at 46° C.). Upon homogenization and filter sterilization this formulation was evaluated for gross hemolytic reaction with human blood using the following procedure:

Volunteer healthy blood was collected with heparin by Vacutainer stick. The plasma was initially straw colored and negative for hemolysis. Drops of whole blood and the drug-free emulsion were brought together under coverslip and observed microscopically for several minutes. During contact, red blood cells (RBCs) remained normocytic. No obvious aggregation of the emulsion particles was noted. No gross changes in platelet or WBC morphology were noted. Then, in test tubes, whole blood and vehicle were mixed 1:1 and 5:1, v/v. As a control whole blood was mixed with saline for injection 1:1. All mixtures were incubated at 37° C. and examined at 10 and 30 min. Supernatants in all three tubes were straw colored and clear. It can be concluded form this study that there is no immediate gross hemolytic reaction between the emulsion vehicle and blood. This suggests that the morphology of the red cell membranes is not perturbed by the surfactants present in the emulsion, in contrast to several reports in the literature on surfactant-induced hemolysis of RBC.

Example 43

Physical Stability Data

Table 16 shows long-term stability of the scaled up formulation of Example 41 upon a 9-month storage at 4° C. or 25° C. It is evident that at least during this storage time, both the mean droplet diameter and the 99% cumulative distribution did not significantly changed from their initial values of about 65 and 150 nm, respectively, and the emulsion remains within specifications.

TABLE 16

Physical Stability of QW8184

| Storage Time (months) | Mean Droplet Diameter, nm (mean ± sd) 4° C. | 25° C. | 99% Cumulative Distribution, nm (mean ± sd) 4° C. | 25° C. |
|---|---|---|---|---|
| 0.0 | 64 ± 0.8 | 63 ± 2.1 | 150 ± 0.7 | 150 ± 0.7 |
| 0.5 | 67 ± 2.9 | 63 ± 2.5 | 152 ± 2.8 | 149 ± 3.6 |
| 1.1 | 64 ± 2.5 | 65 ± 2.5 | 149 ± 2.0 | 152 ± 2.1 |
| 3.1 | 66 ± 1.2 | 62 ± 2.0 | 150 ± 1.2 | 148 ± 2.5 |
| 6.1 | 63 ± 1.2 | 64 ± 3.1 | 150 ± 1.5 | 152 ± 4.0 |
| 9.2 | 64 ± 2.1 | 62 ± 1.0 | 152 ± 2.1 | 153 ± 0.7 |

Example 44

Chemical Stability

A 9-month chemical stability data of the scaled up formulation of Example 41 in terms of paclitaxel potency and levels of known degradants are shown in Tables 17 and 18. As can be seen from these results, there were no significant changes in either the drug potency or the levels of known degradants and the product remains within specifications at both storage temperatures.

TABLE 17

Paclitaxel Potency and Degradants at 4° C.

| Storage Time (months) | Paclitaxel Potency mean ± sd, n = 3 (mg/ML) | Degradants (%, mean ± sd, n = 3) 7-Epi-paclitaxel | Baccatin-3 | 10-Deacetyl-paclitaxel |
|---|---|---|---|---|
| 0.0 | 8.22 ± 0.64 | 0.17 ± 0.01 | 0.12 ± 0.01 | 0.15 ± 0.01 |
| 0.5 | 9.48 ± 0.08 | 0.32 ± 0.05 | 0.15 ± 0.00 | 0.16 ± 0.00 |
| 1.1 | 8.79 ± 0.53 | 0.31 ± 0.03 | 0.17 ± 0.00 | 0.17 ± 0.00 |
| 3.1 | 9.50 ± 0.07 | 0.61 ± 0.03 | 0.20 ± 0.00 | 0.20 ± 0.00 |
| 6.1 | 9.27 ± 0.17 | 0.28 ± 0.02 | 0.17 ± 0.01 | 0.18 ± 0.02 |
| 9.2 | 9.21 ± 0.12 | 0.36 ± 0.02 | 0.17 ± 0.00 | 0.18 ± 0.01 |

TABLE 18

Paclitaxel Potency and Degradants at 25° C.

| Storage Time (months) | Paclitaxel Potency mean ± sd, n = 3 (mg/ML) | Degradants (%, mean ± sd, n = 3) 7-Epi-paclitaxel | Baccatin-3 | 10-Deacetyl-paclitaxel |
|---|---|---|---|---|
| 0.0 | 8.22 ± 0.64 | 0.17 ± 0.01 | 0.12 ± 0.01 | 0.15 ± 0.01 |
| 0.5 | 9.10 ± 0.65 | 0.33 ± 0.00 | 0.17 ± 0.00 | 0.17 ± 0.01 |
| 1.1 | 8.06 ± 0.75 | 0.32 ± 0.04 | 0.17 ± 0.00 | 0.17 ± 0.01 |
| 3.1 | 9.19 ± 0.79 | 0.65 ± 0.05 | 0.22 ± 0.00 | 0.22 ± 0.00 |
| 6.1 | 9.11 ± 0.71 | 0.33 ± 0.02 | 0.16 ± 0.02 | 0.15 ± 0.03 |
| 9.2 | 9.02 ± 0.68 | 0.36 ± 0.02 | 0.18 ± 0.01 | 0.18 ± 0.01 |

Example 45

Efficacy Evaluation

The formulation of Example 41 was evaluated for efficacy against B16 melanoma as described in Examples 18, 19 and 37 and the results are summarized in Table 18.

TABLE 19

Antitumor Activity of QW8184 vs Taxol ® in the B16 Melanoma Model

| Test Article | Dose mg/kg n = 8 | Schedule Days | Survival (mean ± SD) days | % T/C[a] day 20 | % TGI[b] day 20 | T-C[c] days | Log Cell Kill[d] |
|---|---|---|---|---|---|---|---|
| Saline | Control | q3dx5 | 17 ± 2 | — | — | — | — |
| Vehicle | Control | q3dx5 | 20 ± 1 | 93 | 3 | 3 | — |
| Taxol ® | 20 | q3dx5 | 19 ± 5 | 77 | 23 | 3 | 0.5 |
| QW8184 | 20 | q3dx5 | 28 ± 7 | 11 | 89 | 10 | 1.8 |
| QW8184 | 40 | q3dx5 | 33 ± 5 | 0 | 100 | 17 | 3.0 |

[a] % T/C = (Median Tumor Wt of treated/Median Tumor Wt of control) × 100
[b] % TGI = 100 − (% T/C)
[c] T-C = Tumor Growth Delay Value (median time for the treatment group (T) and control (C) to reach a predetermined size (>750 mg)
[d] Log Cell Kill = (T-C value)/(3.32 × tumor doubling time)

By all end points of efficacy, QW8184 exhibited superior antitumor activity in mice at doses that included or well exceeded the MTD of Taxol® but which were well tolerated. Such effects have not been reported with previous injectable emulsions of paclitaxel. MTD is the maximum tolerated dose that is determined from acute toxicity studies.

Example 46

Efficacy Evaluation

The antitumor activity of QW8184 (Example 41), against the human ovarian tumor xenograft IGROV-1 using the marketed product Taxol® as a reference formulation. Nude mice were implanted subcutaneously by trocar with fragments of IGROV-1 human ovarian carcinomas harvested from subcutaneously growing tumors in nude mice hosts. When tumors were approximately 5×5 mm in size, the animals were paired matched into treatment and control groups contained 9 ear-tagged tumor-bearing mice per group. QW8184 was administered i.v. on a q3dx5, q4dx5, and qdx5 schedule at 20, 40 and 60 mg/kg. Taxol® was administered i.v. on the same schedules at 20 mg/kg its maximum tolerated dose. Mice were weighed twice weekly, and tumor measurements were taken by calipers starting Day 1 and converted to mg tumor weight. The experiment was terminated when the control tumors reached approximately 1 gr and tumors were excised and weighed and the mean tumor weight per group was calculated. The data is summarized in. Table 20.

TABLE 20

Antitumor Activity of QW8184 vs Taxol ® in the IGROV-1 Human Ovarian Tumor Xenograft

| Group | Schedule | Dose (mg/kg) | Final Tumor Wt (Mean ± SEM, mg) | % TGI | Mice with Complete Shrinkage |
|---|---|---|---|---|---|
| Saline | q3dx5 | control | 874.8 ± 178.6 | — | 0 |
| QW8184 | q3dx5 | vehicle | 839.9 ± 80.4 | 4.4 | 0 |
| QW8184 | q3dx5 | 20 | 115.9 ± 39.1 | 93.4 | 2 |
| QW8184 | q3dx5 | 40 | 0.1 ± 0.1 | — | 8 |
| QW8184 | q3dx5 | 60 | 0.0 ± 0.0 | — | 7 |
| QW8184 | q4dx5 | 20 | 69.2 ± 28.4 | 99.9 | 3 |
| QW8184 | q4dx5 | 40 | 0.0 ± 0.0 | — | 9 |
| QW8184 | q4dx5 | 60 | 4.9 ± 4.9 | — | 8 |
| QW8184 | qdx5 | 20 | 158.2 ± 56.7 | 88.7 | 3 |
| Taxol ® | q3dx5 | 20 | 22.3 ± 14.2 | — | 3 |
| Taxol ® | q4dx5 | 20 | 24.0 ± 11.5 | — | 3 |
| Taxol ® | qdx5 | 20 | 16.7 ± 9.6 | — | 2 |

Administration of QW8184 at 20, 40 and 60 mg/kg on a q3dx5 or q4dx5 schedule resulted in nearly 100% tumor growth inhibition at all doses with 2, 8, and 7 and 3, 9, and 8 complete tumor responses, respectively. In comparison, administration of Taxol® resulted in 3 complete tumor responses on both schedules. On a qdx5 schedule, the antitumor activities of QW8184 and Taxol® were similar. QW8184, however, was better tolerated with no toxic deaths whereas six toxic deaths were noted with Taxol®. QW8184 was highly active against the IGROV-1 human ovarian xenograft model in a dose-dependent fashion, regardless of the dosing schedule and it was better tolerated than Taxol®.

Example 47

Pharmacokinetic Study

The pharmacokinetics of the formulation of Example 41 (QW8184), in the rat upon a single 10 mg/kg i.v. administration was determined using Taxol® as a reference formulation. The drug was administered i.v. to male or female rats either as a 3-hr infusion (Taxol®) or as a bolus dose (QW8184). Blood samples were collected from 0–72 hrs after dose administration, plasma was prepared by centrifugation and analyzed for paclitaxel concentration using a high performance liquid chromatography (HPLC) method with LC/MS/MS detection. Pharmacokinetic analysis was performed on the mean composite plasma concentration-time profiles using a model independent method. The derived pharmacokinetic parameters are shown in Table 21. The pharmacokinetic parameters determined were as follows:

$T_{max}$: time required to reach peak plasma levels ($C_{max}$)

$C_{max}$: peak plasma concentration of the drug $AUC_{O-t}$: non-extrapolated area under the plasma concentration-time curve from time zero to time t which is the end of the plasma sample collection $AUC_{0-28}$: extrapolated area under the plasma concentration-time curve from time zero to infinite $K_e$: elimination rate constant $T_{1/2}$: elimination half-life $V_d$: Volume of distribution CL: plasma clearance $V_{ss}$: volume of distribution at steady state

TABLE 21

Derived Pharmacokinetic Parameters of Paclitaxel Following Intravenous Administration of QW8184 or Taxol ® in Rats at 10 mg/kg (70 mg/m²)

| Pharmacokinetic Parameter | QW8184 | | Taxol ® | |
|---|---|---|---|---|
| | Male | Female | Male | Female |
| $T_{max}$ (hr) | 0.083 | 0.083 | 3 | 3 |
| $C_{max}$ (ng/mL) | 58950 | 53900 | 5867 | 7227 |
| $AUC_{0-1}$ (ng · hr/mL) | 35504 | 32761 | 18138 | 22701 |
| $AUC_{0-\infty}$ (ng · hr/mL) | 35551 | 32829 | 18347 | 23002 |
| $K_e$ (hr$^{-1}$) | 0.0940 | 0.1375 | 0.1283 | 0.0754 |
| $T_{1/2}$ (hr) | 7.38 | 5.04 | 5.40 | 9.20 |
| $V_d$ (L/kg) | 2.99 | 2.22 | 4.25 | 5.77 |
| CL (L/hr/kg) | 0.281 | 0.305 | 0.545 | 0.435 |
| $V_{ss}$ (L/kg) | 0.228 | 0.242 | 1.44 | 1.09 |

Both the $C_{max}$ and $AUC_{0\to\infty}$ values following the i.v. bolus administration of QW8184 were significantly higher than the corresponding values following the i.v. infusion of Taxol®. The terminal $T_{1/2}$ of paclitaxel in plasma were similar for the two treatments. Tissue binding was more extensive with Taxol® than QW8184 as indicated from differences in the volume of distribution at steady state (Vss). No significant differences in the pharmacokinetic parameters of paclitaxel were observed between male and female animals.

We claim:

1. A composition, comprising:
   one or more tocopherols or derivatives thereof;
   a co-solvent;
   a tocopherol polyethylene glycol succinate;
   an aqueous phase; and
   a chemotherapeutic agent, wherein the chemotherapeutic agent is at least one of a taxoid, a taxine, a microtubule-binding agent, or a taxane;
   wherein the composition is substantially free of any monohydric alcohol, wherein the composition is an emulsion or a microemulsion having an oil and a water phase, and wherein all of the chemotherapeutic agent is in the oil phase.

2. The composition of claim 1, wherein the co-solvent is at least one of dimethylsulfoxide, dimethylamide, ethylene glycol, propylene glycol, glycerol, sorbitol, mannitol, polyethylene glycol, N-methyl-2-pyrrolidone, or pylyvinylpyrrolidone.

3. The composition of claim 2, wherein the polyethylene glycol has a molecular weight between 100 to 10,000.

4. The composition of claim 1, wherein the tocopherol is at least one of α-tocotrienol, β-tocotrienol, γ-tocotrienol, δ-tocotrienol, α-tocopherol, α-tocopherol acetate, α-tocopherol phosphate, α-tocopherol succinate, α-tocopherol nicotinate, or α-tocopherol linoleate.

5. The composition of claim 1, wherein the tocopherol polyethylene glycol succinate is an ester or an ether of α-tocopherol and polyethylene glycol.

6. The composition of claim 1, wherein the tocopherol polyethylene glycol succinate is D-α-tocopherol polyethylene glycol 1000 succinate.

7. The composition of claim 1, wherein the ratio of tocopherol to tocopherol polyethylene glycol derivative is from about 1:1 to about 10:1 w/w.

8. The composition of claim 1 further comprising a surfactant having an HLB of at least 10.

9. The composition of claim 8, wherein the surfactant is at least one of an anionic, cationic, a nonionic, or a zwitterionic surfactant.

10. The composition of claim 8, wherein the surfactant is at least one of a polyoxypropylene-polyoxyethylene glycol nonionic block polymer, ascorbyl-6-palmitate, stearylamine, or a sucrose fatty ester.

11. The composition of claim 8, wherein the surfactant is pegylated.

12. The composition of claim 8, wherein the surfactant has the structure:

$$H(OCH_2CH_2)_a(OC_3H_6)_b(OCH_2CH2)_aOH$$

wherein a is 101 and b is 56.

13. The composition of claim 1, wherein the taxane is paclitaxel.

14. The composition of claim 1, wherein the monohydric alcohol is at least one of ethanol, butanol, or isopropanol.

15. A pharmaceutical composition, consisting essentially of: paclitaxel,
   one or more tocopherols or derivatives thereof,
   a tocopherol polyethylene glycol derivative,
   polyethylene glycol,
   a polyoxypropylene-polyoxyethylene glycol nonionic block polymer, and an aqueous phase.

16. The composition of claim 15, wherein the tocopherol is at least one of α-tocotrienol, β-tocotrienol, γ-tocotrienol, δ-tocotrienol, α-tocopherol, α-tocopherol acetate, α-tocopherol phosphate, α-tocopherol succinate, α-tocopherol nicotinate, or α-tocopherol linoleate.

17. The composition of claim 15, wherein the tocopherol is α-tocopherol.

18. The composition of claim 15, wherein the tocopherol polyethylene glycol derivative is a tocopherol polyethylene glycol succinate.

19. The composition of claim 18, wherein the tocopherol polyethylene glycol succinate is an ester or an ether of α-tocopherol and polyethylene glycol.

20. The composition of claim 18, wherein the tocopherol polyethylene glycol succinate is D-α-tocopherol polyethylene glycol 1000 succinate.

21. The composition of claim 15, wherein the polyethylene glycol has a molecular weight between 100 to 100,000.

22. The composition of claim 15, wherein the block polymer has the structure:

$$H(OCH_2CH_2)_a(OC_3H_6)_b(OCH_2CH_2)_aOH$$

wherein a is 101 and b is 56.

* * * * *

UNITED STATES PATENT AND TRADEMARK OFFICE
CERTIFICATE OF CORRECTION

PATENT NO. : 6,660,286 B1
DATED : December 9, 2003
INVENTOR(S) : K.J. Lambert et al.

It is certified that error appears in the above-identified patent and that said Letters Patent is hereby corrected as shown below:

Column 40,
Line 21, "$(OCH_2CH2)_a$" should read -- $(OCH_2CH_2)_a$ --

Signed and Sealed this

Twenty-seventh Day of July, 2004

JON W. DUDAS
*Acting Director of the United States Patent and Trademark Office*